US011937937B2

(12) United States Patent
Leung et al.

(10) Patent No.: US 11,937,937 B2
(45) Date of Patent: Mar. 26, 2024

(54) METHODS OF IDENTIFYING ATOPIC DERMATITIS AND FOOD ALLERGIES

(71) Applicant: National Jewish Health, Denver, CO (US)

(72) Inventors: Donald Leung, Denver, CO (US); Elena Goleva, Denver, CO (US); Evgeny Berdyshev, Littleton, CO (US)

(73) Assignee: National Jewish Health, Denver, CO (US)

( * ) Notice: Subject to any disclaimer, the term of this patent is extended or adjusted under 35 U.S.C. 154(b) by 689 days.

(21) Appl. No.: 16/654,333

(22) Filed: Oct. 16, 2019

(65) Prior Publication Data
US 2020/0113508 A1 Apr. 16, 2020

Related U.S. Application Data

(60) Provisional application No. 62/746,313, filed on Oct. 16, 2018.

(51) Int. Cl.
A61B 5/00 (2006.01)
(52) U.S. Cl.
CPC .................... A61B 5/443 (2013.01)
(58) Field of Classification Search
CPC ........................................................ A61B 5/443
See application file for complete search history.

(56) References Cited

U.S. PATENT DOCUMENTS

| 2005/0065539 | A1* | 3/2005 | Muser ............... C12M 33/00 606/161 |
| 2012/0065086 | A1* | 3/2012 | Benson ............. G01N 1/2813 435/6.12 |
| 2017/0166894 | A1* | 6/2017 | Demock ............ C12N 15/115 |
| 2019/0302133 | A1* | 3/2019 | Ishikawa ........... G01N 33/92 |

FOREIGN PATENT DOCUMENTS

| JP | 2001161697 A | * | 6/2001 |
| JP | 2017181143 A | * | 10/2017 |
| WO | WO 2004/016785 | | 2/2004 |
| WO | WO 2017/220763 | | 12/2017 |

OTHER PUBLICATIONS

Yohei Egawa, Kenji Kabashima, Barrier dysfunction in the skin allergy, Allergology International, vol. 67, Issue 1, ISSN 1323-8930, https://doi.org/10.1016/j.alit.2017.10.002. (Year: 2017).*

Cole C, Kroboth K. Filaggrin-stratified transcriptomic analysis of pediatric skin identifies mechanistic pathways in patients with atopic dermatitis. J Allergy Clin Immunol. Jul. 2014; 134(1):82-91. doi: 10.1016/j.jaci.2014.04.021. Epub May 28, 2014. PMID: 24880632; PMCID: PMC4090750. (Year: 2014).*

(Continued)

Primary Examiner — Puya Agahi
Assistant Examiner — Grace L Rozanski
(74) Attorney, Agent, or Firm — Sheridan Ross P.C.

(57) ABSTRACT

The invention relates to skin tape stripping methods to identify a subject at risk of having atopic dermatitis, or a subject having atopic dermatitis who is at risk of developing a food allergy, or a subject at risk of developing a food allergy in the absence of the subject having atopic dermatitis.

11 Claims, 13 Drawing Sheets

(56) References Cited

OTHER PUBLICATIONS

Choi MJ, Maibach HI. Role of ceramides in barrier function of healthy and diseased skin. Am J Clin Dermatol. 2005;6(4):215-23. doi: 10.2165/00128071-200506040-00002. PMID: 16060709. (Year: 2005).*

"Food allergy," Wikipedia, edited May 16, 2018, 22 pages [retrieved online from: en.wikipedia.org/w/index.php?title=Food_allergy&oldid=841610064].

"Stratum Corneum," Wikipedia, edited Nov. 2017, 3 pages [retrieved online from: en.wikipedia.org/w/index.php?title=Stratum_corneum&oldid=808383480].

Egawa et al. "Barrier dysfunction in the skin allergy," Allergology International, 2018, vol. 67, pp. 3-11.

International Search Report and Written Opinion for International (PCT) Patent Application No. PCT/US19/56505, dated Feb. 19, 2020 16 pages.

International Preliminary Report on Patentability for International (PCT) Patent Application No. PCT/US2019/056505, dated Apr. 29, 2021 12 pages.

* cited by examiner

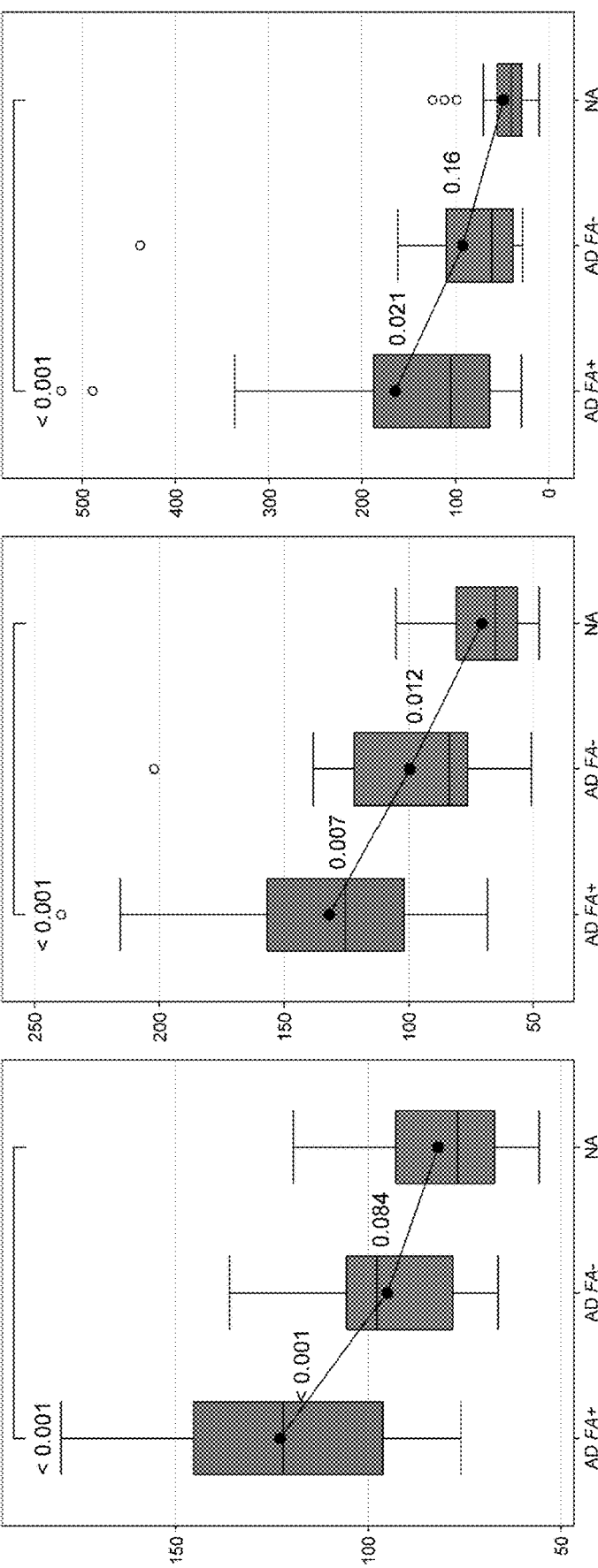

METHODS OF IDENTIFYING ATOPIC DERMATITIS AND FOOD ALLERGIES

CROSS-REFERENCE TO RELATED APPLICATIONS

This application claims the benefit of priority under 35 U.S.C. § 119(e) to U.S. Provisional Patent Application No. 62/746,313, filed Oct. 16, 2018. The entire disclosure of U.S. Provisional Patent Application No. 62/746,313 is incorporated herein by reference.

GOVERNMENT SUPPORT

This invention was made with government support under grant number U19 AI117673 awarded by the National Institutes of Health. The government has certain rights in the invention.

BACKGROUND OF THE INVENTION

Atopic dermatitis (AD) is the most common inflammatory skin disease in childhood affecting nearly 20% of children (Czarnowicki T. Novel concepts of prevention and treatment of atopic dermatitis through barrier and immune manipulations with implications for the atopic march. J Allergy Clin Immunol 2017; 139:1723-34). It is associated with severe itching, sleep disturbance, significant impairment of quality of life, and allergen sensitization that result in complex clinical features (Klinnert M D, Booster G, Copeland M, et al. Role of behavioral health in management of pediatric atopic dermatitis. Ann Allergy Asthma Immunol 2018; 120: 42-8 e8). A major dichotomy between AD patients involves the distinction between highly allergic (also referred to as extrinsic AD) versus non-allergic AD (also referred to as intrinsic AD). AD patients with multiple allergen sensitization to foods and aeroallergens often undergo the so-called atopic march which classically progresses from AD to food allergy (FA) and respiratory allergy (Tran M M. Predicting the atopic march: Results from the Canadian Health Infant Longitudinal Development Study. J Allergy Clin Immunol 2018; 141:601-7). There is enormous interest in identifying the different endotypes and skin biomarkers which result in various clinical phenotypes of AD in the hope that this will translate into personalized treatments with improved outcomes beyond what is achieved with current non-specific approaches (Muraro A, Lemanske R F, Jr., Hellings P W, et al. Precision medicine in patients with allergic diseases: Airway diseases and atopic dermatitis-PRACTALL document of the European Academy of Allergy and Clinical Immunology and the American Academy of Allergy, Asthma & Immunology. J Allergy Clin Immunol 2016; 137:1347-58). Although blood biomarkers can correlate with AD disease activity, their interpretation is limited by potential contribution within the circulation from allergic co-morbidities such as asthma, allergic rhinitis, and FA. Skin biopsies are invasive and not accepted by most study participants.

Food allergy only affects one-third of children with AD, with allergy to peanuts, egg, and milk as the predominant food allergies (Eigenmann P A. Prevalence of IgE-mediated food allergy among children with atopic dermatitis. Pediatrics 1998; 101:e8). These patients are at great risk for severe allergic reactions to environmental foods and have a restricted diet accompanied by poor quality of life. Recent studies have demonstrated that both peanut allergy and AD are strongly associated with filaggrin (FLG) gene mutations (Brough H A, Simpson A, Makinson K, et al. Peanut allergy: effect of environmental peanut exposure in children with filaggrin loss-of-function mutations. J Allergy Clin Immunol 2014; 134:867-75 e1). Although only a minority of AD and FA patients have FLG gene mutations, this strong association suggests skin barrier dysfunction contributes to the development of both AD and FA (Irvine A D. Filaggrin mutations: Associations with skin and allergic diseases. N Engl J Med 2011; 365:1315-27). Indeed, previous studies have reported that the strongest risk factors for the development of peanut allergy in children are the epicutaneous application of peanut-containing creams or oils, skin infection, and severity of AD (Lack G, Fox D, Northstone K, Golding J, Avon Longitudinal Study of P, Children Study T. Factors associated with the development of peanut allergy, in childhood. N Engl J Med 2003; 348:977-85; Tordesillas L, Goswami R, Benede S, et al. Skin exposure promotes a Th2-dependent sensitization to peanut allergens. J Clin Invest 2014; 124:4965-75). Non-lesional AD skin has not been comprehensively evaluated in AD FA+ participants.

As disclosed herein, the most superficial compartment (*Stratum corneum*) of non-lesional skin in individuals with AD and food allergy, but not in individuals with AD without food allergy or non-atopic individuals, is associated with a constellation of *Stratum corneum* biomarkers that are indicative of an immature skin barrier and increased Type 2 immune activation.

SUMMARY OF THE INVENTION

One embodiment of the invention relates to a method to identify a subject at risk of developing atopic dermatitis comprising: (a) obtaining a skin sample from the subject, wherein the skin sample is a non-lesional skin sample from the subject; (b) determining the level of one or more filaggrin breakdown products selected from the group consisting of urocanic acid (UCA), pyroglutamic (PCA) and a combination thereof; and (c) comparing the level of the one or more filaggrin breakdown products in the skin sample to a control sample wherein a statistically different level in the skin sample as compared to the same filaggrin breakdown product in the control sample identifies the subject as being at risk of developing atopic dermatitis, and wherein the control sample is from one or more non-atopic (NA) subjects.

Another embodiment of the invention relates to a method to identify a subject having atopic dermatitis at risk of developing a food allergy comprising: (a) obtaining a skin sample from the subject, wherein the skin sample is a non-lesional skin sample from the subject; (b) determining the level of one or more filaggrin breakdown products selected from the group consisting of urocanic acid (UCA), pyroglutamic (PCA) and a combination thereof; and (c) comparing the level of the one or more filaggrin breakdown products in the skin sample to a control sample wherein a statistically different level in the skin sample as compared to the same filaggrin breakdown product in the control sample identifies the subject as being at risk of developing a food allergy, and wherein the control sample is from one or more subjects having atopic dermatitis without having a food allergy. In one aspect of this method, the skin sample comprises layers 15, 16 or the sum layers 15 and 16 of from the *Stratum corneum* of the subject.

Another embodiment of the invention relates to a method to identify a subject at risk of developing a food allergy comprising: (a) obtaining a skin sample from the subject, wherein the skin sample is a non-lesional skin sample from the subject; (b) determining the level of one or more filaggrin breakdown products selected from the group consisting of urocanic acid (UCA), pyroglutamic (PCA) and a combination thereof; and (c) comparing the level of the one or more filaggrin breakdown products in the skin sample to a control sample wherein a statistically different level in the skin sample as compared to the same filaggrin breakdown product in the control sample identifies the subject as being at risk of developing a food allergy, and wherein the control sample is from one or more non-atopic (NA) subjects. In one aspect of this method, the subject does not have atopic dermatitis.

Another embodiment of the invention relates to a method to identify a subject at risk of having atopic dermatitis comprising: (a) obtaining a skin sample from the subject, wherein the skin sample is a non-lesional skin sample from the subject; (b) determining the expression level of one or more proteins selected from the group consisting of serpin family B member 12 (SERPINB12), keratin 77 (KRT77), N-Acylsphingosine Amidohydrolase 1 (ASAH1), and cystatin A (CSTA), in the skin sample; and (c) comparing the expression level of the one or more proteins in step b to a control sample, wherein a statistically different expression level of the one or more proteins from step b as compared to the expression level of the same one or more proteins in the control sample identifies the subject as being at risk of having atopic dermatitis, and wherein the control sample is from one or more non-atopic (NA) subjects. In one aspect of this method, the expression level of one or more proteins selected from the group consisting of SERPINB12, KRT77, ASAH1, CSTA, is significantly decreased as compared to the control levels.

Another embodiment of the invention relates to a method to identify a subject having atopic dermatitis at risk of developing a food allergy comprising: (s) obtaining a skin sample from the subject, wherein the skin sample is a non-lesional skin sample from the subject; (b) determining the expression level of one or more proteins selected from the group consisting of Keratin 14 (KRT14), Keratin 5 (KRT5), Keratin 16 (KRT16), enolase 1 (ENO1), gluthathione S-transferase Pi 1 (GSTP1), desmoplakin (DSP), actin B (ACTB), eukariotic translational elongation factor 1 alpha 1 (EEF1A1), GDP dissociation inhibitor 2 (GDI2), gelsolin (GSN), histone H2B type 1-K (HISTH2BK), histone H3.1 (HIST1H3), histone H4 (HIST1H4), heat shock protein B 1 (HSPB1), lactic dehydrtogenase A (LDHA), galectin 3 (LGALS3), galectin 7 (LGALS7), POF1B actin binding protein (POF1B), S100 calcium binding protein A7 (S100A7), S100 calcium binding protein A8 (S100A8), S100 calcium binding protein A9 (S100A9), serpin family B member 3 (SERPINB3), stratifin (SFN), small prolin rich protein 1 A (SPRR1A), small proline rich protein 2 D (SPRR2D), tubulin alpha 1 B chain (TUB1 AB) and ALMS1 centrosome and basal body associated protein (ALMS1) in the skin sample; and (c) comparing the expression level of the one or more proteins in step b to a control sample, wherein a statistically different expression level of the one or more proteins from step b as compared to the expression level of the same one or more proteins in the control sample identifies the subject as being at risk of the subject as being at risk of developing a food allergy, and wherein the control sample is from one or more subjects having atopic dermatitis without having a food allergy. In one aspect of this method, the expression level of one or more proteins selected from the group consisting of KRT14, KRT5, KRT16, ACTB, DSP, EEF1A1, ENO1, GDI2, GSN, GSTP1, HISTH2BK, HIST1H3, HIST1H4, HSPB1, LDHA, LGALS, LGALS3, POF1B, S100A7, S100A8, S100A9, SERPINB3, SFN, SPRR1A, SPRR2D, TUB1A, and ALMS1, is significantly increased as compared to the control levels.

In one aspect of any of the embodiments related to a method, the method further comprises determining the ratio of esterified co-hydroxy fatty acid sphingosine ceramides (EOS CER) to nonhydroxy fatty acid sphingosine ceramides (NS CER) in the skin sample from the subject; and comparing the ratio of EOS CER to NS CER in the skin sample to a control sample wherein a decreased ratio in the skin sample as compared to the control sample further identifies the subject as being at risk of developing a food allergy.

In one aspect of any of the embodiments related to a method, the skin sample comprises layers 1, 2 or the sum of layers 1 and 2 from the *Stratum corneum* of the subject.

In one aspect of any of the embodiments related to a method, the skin sample comprises layers 3, 4 or the sum of layers 3 and 4 from the *Stratum corneum* of the subject.

In one aspect of any of the embodiments related to a method, the skin sample is obtained by a skin tape stripping method. In one aspect, the skin tape stripping method comprises applying an adhesive tape to a target area of the skin of the subject in a manner sufficient to isolate an epidermal sample adhering to the adhesive tape, wherein the epidermal sample comprises cells from the *Stratum corneum* of the subject, and wherein the tape comprises a rubber adhesive; and extracting the epidermal sample adhering to the adhesive tape with a cell scraper comprising thermoplastic elastomer material in a solvent of about 5% to about 30% alcohol in water. In one aspect, the method further comprising determining the expression level of the one or more proteins and/or the one or more filaggrin breakdown products in the epidermal sample.

In one aspect of any of the embodiments related to a method, the subject identified as at risk of developing atopic dermatitis or at risk of developing a food allergy is administered a composition comprising a compound selected from the group consisting of corticosteroids, leukotriene antagonists, anti-cytokine antibodies, anti-cytokine receptor antibodies, anti-IgE antibody, anti-interleukin 14 (IL14) antibodies, anti-interleukin 13 (IL13) antibodies, JAK kinase inhibitors, JAK/STAT inhibitors, antibiotics, a phosphodiesterase inhibitor, a cream comprising filaggrin or components thereof, ceramide rich emollients, and combinations thereof. In one aspect, the composition is administered to the subject by an administration route selected from the group consisting of local administration, topical administration, and injection.

In one aspect of any of the embodiments related to a method, the food allergy is selected from the group consisting of a peanut allergy, a milk allergy, an egg allergy, a wheat allergy, a tree nut allergy and combinations thereof. In one aspect, the food allergy is a peanut allergy.

In one aspect of any of the embodiments related to a method, the subject is less than 18 years of age.

BRIEF DESCRIPTION OF THE DRAWINGS

FIGS. 2A-2C show Keratin (KRT) expression in non-lesional skin. Comparisons between groups for markers of keratin expression: KRT 5 (FIG. 2A), KRT 14 (FIG. 2B), and KRT 16 (FIG. 2C) in non-lesional skin. Protein extracts were prepared from 15 skin tapes combined. Note the complete separation between AD FA+vs AD FA−vs NA for KRT14. In the boxplot, the solid horizontal line represents the median and the filled circle represents the mean. The box margins are the interquartile range, and the whiskers extend 1.5 times the interquartile range. Observations outside the whisker are marked by a hollow circle. The annotations are the p-values from pairwise comparisons between groups.

DETAILED DESCRIPTION OF THE INVENTION

Figure 1A:
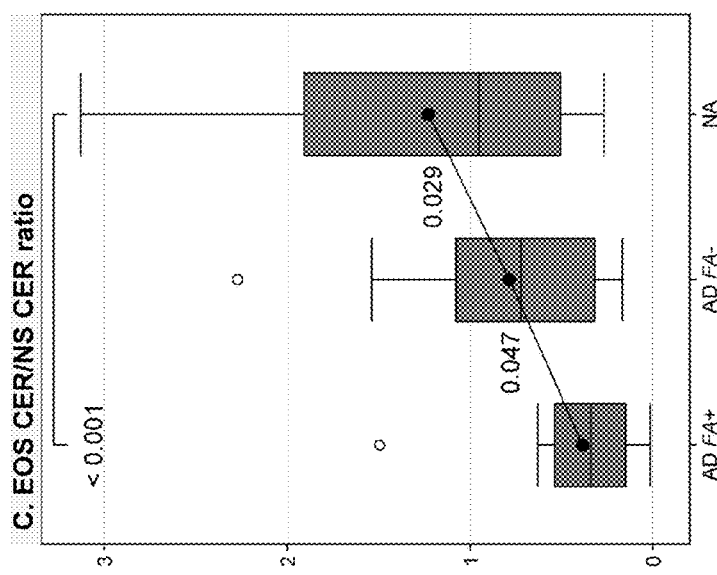
FIGS. 1A, 1B and 1C show filaggrin breakdown products and the proportion of co-hydroxy fatty acid (EO) sphingosine (S) ceramides (CER) which are ultra long chained ceramides (EOS CER) content in non-lesional skin. Comparisons between groups for filaggrin breakdown products total urocanic acid (UCA) (FIG. 1A), pyroglutamic acid (FIG. 1B), and EOS CER/NS CER ratio (FIG. 1C) all assessed at skin tapes #15-16 on non-lesional skin. Note the complete separation between AD FA+vs AD FA−vs NA at skin tapes #15-16 for total UCA and EOS CER/NS CER ratio. In the boxplot, the solid horizontal line represents the median and the filled circle the mean. The box margins are the interquartile range, and the whiskers extend 1.5 times the interquartile range. Observations outside the whisker are marked by a hollow circle. The annotations are the p-values from pairwise comparisons between groups.

As disclosed herein the inventors used a novel, minimally invasive skin tape strip (STS) measure of the *Stratum corneum* (SC) to determine whether AD FA+ children have skin biomarkers which distinguish them from AD FA− and NA (non-atopic, healthy) children. Despite similar skin disease severity, the FLG content was significantly lower in children who were AD FA+ as compared to AD FA−. Lipid profiling of the SC in the AD FA+ group revealed a relative reduction in esterified ω-hydroxy fatty acid (EO) sphingosine (S) ceramides (CER) which are ultra long chained ceramides (EOS CER) required for normal skin barrier function. At the same time, a significant increase in nonhydroxy fatty acid sphingosine (NS) ceramide levels was observed in AD FA+ skin samples, resulting in a disproportionate decrease in EOS CER in the skin of these patients. STS proteomics revealed an immature keratin profile consistent with keratinocyte hyperproliferation in the SC of AD FA+ participants. A network analysis demonstrated KRT14, KRT5 and KRT16 expression, as well as reduced FLG breakdown products, were most strongly correlated with AD FA+. These data demonstrate that AD FA+ children exhibit a unique constellation of skin biomarkers, measurable with minimally invasive methods, that distinguish them from AD FA− and NA children. These data support the importance of skin barrier dysfunction in the pathogenesis of epicutaneous sensitization to environmental foods and can contribute to the persistence or severity of FA by chronically stimulating Type 2 immune responses in the skin.

AD FA+ children represent a unique endotype that can be distinguished from AD FA− or NA by a constellation of SC biomarkers including low FLG breakdown products, increased KRT14, and a reduced EOS CER/NS CER ratio. These differences were most pronounced at STS layers #15-20, at the interface between the SC and *Stratum granulosum*, a level at which topical products rarely reach. These findings in the non-lesional skin were not attributable to differences in AD skin severity, because there was no significant difference between the AD FA+ group and the AD FA− group using 3 different clinical skin severity scoring systems (Nottingham Eczema Severity Score (NESS), Eczema Area and Severity Index (EASI), and SCCORing Atopic Dermatitis (SCORAD)). All groups studied were balanced for age, gender, and race to control for potential confounding factors. Lesional skin in the two groups of AD had similar transepidermal water loss (TEWL), FLG breakdown products, and EOS CER content suggesting that distinction between AD FA+vs AD FA− was found only in non-lesional AD skin. Importantly, the reduced levels of FLG breakdown products and EOS CER/NS CER ratio in non-lesional skin of AD FA+ participants approached those observed in lesional AD skin.

Barrier integrity is thought to reflect the function of multiple epidermal proteins and lipids in the *Stratum corneum*. FLG, in particular, is a structural protein that is, critical in controlling water retention in the skin, and the hydroscopic properties of FLG breakdown products play an important role as natural moisturizing factor ingredients (Irvine A D. Filaggrin mutations: Associations with skin and allergic diseases. N Engl J Med 2011; 365:1315-27). FLG gene mutations have been associated with increased TEWL and peanut allergy in Northern Europe. (Brown S J, Asai Y, Cordell H J, et al. Loss-of-function variants in the filaggrin gene are a significant risk factor for peanut allergy. J Allergy Clin Immunol 2011; 127:661-7). Studies in the U.S., however, have not confirmed an important association of FLG mutation with peanut allergy but linked peanut allergy to AD severity (Brough H A. Atopic dermatitis increases the impact of exposure to peanut antigen in dust on peanut sensitization and allergy. J Allergy Clin Immunol 2015; 135:164-70). Epicutaneous sensitization to foods is enhanced in FLG-deficient mice due to increased epidermal allergen penetration leading to type 2 immune activation suggesting an important role for FLG deficiency in FA (Walker M T, Green J E, Ferrie R P, Queener A M, Kaplan M H, Cook-Mills J M. Mechanism for initiation of food allergy: Dependence on skin barrier mutations and environmental allergen co-stimulation. J Allergy Clin Immunol 2018; 141:1711-25 e9). Alternatively, the inventors and others have demonstrated that there are multiple causes of acquired reduction in FLG protein levels (Thyssen J P. Causes of epidermal filaggrin reduction and their role in the pathogenesis of atopic dermatitis. J Allergy Clin Immunol 2014; 134:792-9). Immune activation involving type 2 cytokines, e.g. interleukin 4/interleukin 13 (IL-4/IL-13), interleuking 31 (IL-31), thymic stromal lymphopoietin (TSLP), and interleukin 33 (IL-33) or inflammatory cytokines such as tumor necrosis factor alpha (TNF-α) can cause a significant reduction of FLG (Howell M D. Cytokine modulation of AD filaggrin skin expression. J Allergy Clin Immunol 2007; 120:150-5; Kim B E. Loricrin and involucrin expression is down-regulated by Th2 cytokines through STAT-6.

Clin Immunol 2008; 126:332-7; De Benedetto A, Rafaels N M, McGirt L Y, et al. Tight junction defects in patients with atopic dermatitis. J Allergy Clin Immunol 2011; 127:773-86 e1-7).

As disclosed herein, the inventors have determined that there is low FLG breakdown product content in the skin at STS #5-6 in both the AD FA+ and AD FA− groups confirming the importance of FLG in AD, in general. Still a further novel aspect is the finding that at STS #15-16, there is significant separation between the AD FA+, AD FA−, and NA groups such that deeper levels of the skin AD FA+ had the most profound defect in skin barrier. Additionally, side by side comparisons between STS and skin biopsies were used to assess depth of sampling, and the findings revealed that STS #15-20 reach the *Stratum granulosum* where viable cells including Langerhans cells and keratinocytes exist.

FLG plays a critical role in keratinocyte differentiation including lipid transport into the extracellular space around keratinocytes (Pendaries V, Malaisse J, Pellerin L, et al. Knockdown of filaggrin in a three-dimensional reconstructed human epidermis impairs keratinocyte differentiation. J Invest Dermatol 2014; 134:2938-46). FLG deficiency leads to impaired lipid profile and altered acidification pathways (Vavrova K, Henkes D, Struver K, et al. Filaggrin deficiency leads to impaired lipid profile and altered acidification pathways in a 3D skin construct. J Invest Dermatol 2014; 134:746-53). Lipid abnormalities have been reported in patients with FLG mutations (Gruber R, Elias P M, Crumrine D, et al. Filaggrin genotype in ichthyosis vulgaris predicts abnormalities in epidermal structure and function. Am J Pathol 2011; 178:2252-63). Ultra-long chain lipids, such as EOS CER, control water retention in the skin and prevent allergen penetration (Elias P M, Wakefield J S. Mechanisms of abnormal lamellar body secretion and the dysfunctional skin barrier in patients with atopic dermatitis. J Allergy Clin Immunol 2014; 134:781-91 e1). Importantly, modified (oxidized and de-esterified) EOS ceramides and epidermal structural proteins, such as involucrin, loricrin, and periplakin, cross-link to create an impermeable barrier that prevents allergen penetration and water loss, with FLG facilitating structural alignment of cornified envelope proteins (Candi E. The cornified envelope: a model of cell death in the skin. Nat Rev Mol Cell Biol 2005; 6:328-40; Marekov L N, Steinert P M. Ceramides are bound to structural proteins of the human foreskin epidermal cornified cell envelope. J Biol Chem 1998; 273:17763-70). Loss of acidification in the epidermis results in activation of proteases such as kallikrein which damages the skin barrier. Interestingly, Netherton's Syndrome which is associated with increased skin protease activity due to serine peptidase inhibitor, Kazal Type 5 (SPINKS) deficiency is often associated with FA. The inventors have determined that there is a significant decrease in EOS CER/NS CER ratio in STS of AD FA+ participants as compared to the AD FA− and NA groups. Both the low FLG breakdown products and reduced EOS CER were highly correlated with transepidermal water loss area under the curve (TEWL AUC) and food allergen sensitization. The cause of low FLG and EOS CER in AD FA+ children is unknown, however the Inventors believe it is likely due to a complex combination of epidermal structural genetic mutations and cytokine activation. Importantly, the levels of FLG breakdown products and EOS CER in non-lesional STS #15-16 of AD FA+ were not only the lowest among the three study groups, but approached levels seen in lesional skin of AD FA− and AD FA+ participants. The greatest decrease in the ratio between EOS CER and NS CER in AD FA+ children also indicates the maximal loss of skin hydrophobicity due to a decline of highly hydrophobic EOS CER and the increase in short-chain NS CER. This suggests the entire skin surface of AD FA+ subjects is at risk for allergen penetration.

Future interventional birth cohort studies are required in humans to, untangle the web between reduced FLG and EOS CER, increased KRT14, KRT5, KRT16 and food allergen sensitization. Supporting a role for the skin barrier in driving AD and FA, a pilot study with a lipid-rich skin emollient from birth was found to improve skin barrier function and reduce food allergen sensitization (Lowe A J, Su J C, Allen K J, et al. A randomized trial of a barrier lipid replacement strategy for the prevention of atopic dermatitis and allergic sensitization: the PEBBLES pilot study. Br J Dermatol 2018; 178:e19-e21). As novel safe approaches are developed to inhibit type 2 immunity, this will clarify the role that type 2 immunity plays in food allergy (Keet C A. Emerging therapies for food allergy. J Clin Invest 2014; 124:1880-6).

The multi-omics analyses disclosed herein suggests a major role for low FLG level in FA. Unexpectedly, the inventors found increased KRT14 expression patterns in AD FA+ skin suggesting that keratinocytes are hyperproliferating in the epidermis of AD FA+ patients. This impairs terminal differentiation and provides an explanation for impaired skin barrier function in these patients. IL-4/IL-13 have been previously documented to inhibit keratinocyte differentiation in vitro (Omori-Miyake M, Yamashita M, Tsunemi Y, Kawashima M, Yagi J. In vitro assessment of IL-4- or IL-13-mediated changes in the structural components of keratinocytes in mice and humans. J Invest Dermatol 2014; 134:1342-50). Thus, the observed changes in keratin profiles of AD FA+ can be a marker of enhanced type 2 response in the skin of AD FA+ patients.

As provided for in the examples herein, the inventors have performed a comprehensive evaluation of children with AD comparing AD FA+ versus AD FA− with a novel minimally invasive STS sampling technique that allowed anlysis of lipidomics, FLG breakdown products, and proteomics. This analysis by local skin sampling has clear advantages over blood biomarkers that may diffuse from different tissues due to atopic comorbidities. While skin biopsies are informative, the inventors have found that less than 30% of study participants are willing to give skin biopsies; whereas, all study participants willingly provided STS leading to less bias in sample collection (Dyjack N, Goleva E, Rios C, et al. Minimally invasive skin tape strip RNA sequencing identifies novel characteristics of the type 2-high atopic dermatitis disease endotype. J Allergy Clin Immunol 2018; 141:1298-309). The findings not only demonstrate that the AD FA+ group represents a unique AD endotype but identifies a defective *Stratum corneum* as the key abnormality that distinguishes AD FA+ from AD FA− or NA participants. It is important to emphasize that these findings of SC abnormalities were observed in non-lesional healthy-looking AD skin, indicating that these skin changes can be occurring before the occurrence of clinical skin lesions, and thus place the AD FA+ patient at great risk since their entire skin body surface area may be susceptible to food allergen penetration and allergen sensitization. Although previous epidemiology studies in children with peanut allergy and experimental mouse models have implicated epicutaneous allergen sensitization, the inventors are the first to systematically study these intertwined associations and provide a tool(s) to directly demonstrate that the skin of AD FA+ children has a defect in their SC. The data provided herein support the concept that primary and secondary prevention of AD and FA in this subset of AD should focus on improving skin barrier function.

The inventors further demonstrate herein the utility of FLG breakdown products analysis in non-lesioanl superficial skin layers for the identification of subjects with AD, or subjects with FA only and no history of AD. In addition, the inventors also determined a set of proteins with unique expression in subjects of AD FA+ endotype or in AD subjects irrespective of FA.

To establish a primary prevention strategy and/or treatment strategy for allergic diseases, it is important to identify skin biomarkers that can predict the occurrence of allergic diseases such as AD, food allergies, asthma and allergic rhinitis, as well as, to identify subjects having AD and one or more food allergies and subjects having AD without having a food allergy as well.

The present invention provides for a method to identify a subject at risk of developing atopic dermatitis. In one aspect, this method comprises obtaining a skin sample from the subject, wherein the skin sample is a non-lesional skin sample from the subject. In one aspect, the skin sample is from a normal appearing skin that has no rash. In one aspect of this method, the level of one or more filaggrin breakdown products selected from the group consisting of urocanic acid (UCA), pyroglutamic (PCA) and a combination thereof is determined from the skin sample. The level of the one or more filaggrin breakdown products in the skin sample is compared to filaggrin breakdown products from a control sample, wherein a statistically different level in the subject's skin sample as compared to the level of the same filaggrin breakdown products from a control sample identifies the subject as being at risk of developing atopic dermatitis. In one aspect, the control sample is from one or more non-atopic (NA) subjects.

The present invention also provides for a method to identify a subject having atopic dermatitis at risk of developing a food allergy. In one aspect, this method comprises obtaining a skin sample from the subject, wherein the skin sample is a non-lesional skin sample from the subject. In one aspect, the skin sample is from a normal appearing skin that has no rash. In one aspect of this method, the level of one, or more filaggrin breakdown products selected from the group consisting of urocanic acid (UCA), pyroglutamic (PCA) and a combination thereof is determined. The level of the one or more filaggrin breakdown products in the subject's skin sample is compared to the levels of the same filaggrin breakdown products from a control sample, wherein a statistically different level in the skin sample as compared to the same filaggrin breakdown product in the control sample identifies the subject as being at risk of developing a food allergy. In one aspect, the control sample is from one or more subjects having atopic dermatitis without having a food allergy.

The present invention further provides for a method to identify a subject at risk of developing a food allergy. In one aspect, this method comprises obtaining a skin sample from the subject, wherein the skin sample is a non-lesional skin sample from the subject. In one aspect, the skin sample is from a normal appearing skin that has no rash. In one aspect of this method, the level of one or more filaggrin breakdown products selected from the group consisting of urocanic acid (UCA), pyroglutamic (PCA) and a combination thereof is determined. The level of the one or more filaggrin breakdown products in the subject's skin sample is compared to the levels of the same filaggrin breakdown products from a control sample wherein a statistically different level in the skin sample as compared to the same filaggrin breakdown product in the control sample identifies the subject as being at risk of developing a food allergy. In one aspect, the control sample is from one or more non-atopic (NA) subjects. In one aspect, the subject does not have atopic dermatitis.

The present invention also provides for a method to identify a subject at risk of having atopic dermatitis. In one aspect, this method comprises obtaining a skin sample from the subject, wherein the skin sample is a non-lesional skin sample from the subject. In one aspect, the skin sample is from a normal appearing skin that has no rash. In one aspect of this method, the expression level of one or more proteins selected from the group consisting of serpin family B member 12 (SERPINB12), keratin 77 (KRT77), N-Acyl-sphingosine Amidohydrolase 1 (ASAH1), and cystatin A (CSTA), in the skin sample is determined. The expression level of the one or more proteins is compared to the same one or more proteins from a control sample, wherein a statistically different expression level of the one or more proteins from the subject's skin sample as compared to the expression level of the same one or more proteins from the control sample identifies the subject as being at risk of having atopic dermatitis. In one aspect, the expression levels of one or more proteins selected from the group consisting of SERPINB12, KRT77, ASAH1, CSTA is significantly decreased as compared to the control levels. In yet another aspect, the expression levels are decreased about 1.5-fold to about 3-fold (or about 150% to 300% decrease) as compared to the control levels. In one aspect, the control sample is from one or more non-atopic (NA) subjects.

The present invention further provides for a method to identify a subject having atopic dermatitis at risk of developing a food allergy. In one aspect, this method comprises obtaining a skin sample from the subject, wherein the skin sample is a non-lesional skin sample from the subject. In one aspect, the skin sample is from a normal appearing skin that has no rash. In one aspect of this method, the expression level of one or more proteins selected from the group consisting of Keratin 14 (KRT14), Keratin 5 (KRT5), Keratin 16 (KRT16), enolase 1 (ENO1), gluthathione S-transferase Pi 1 (GSTP1), desmoplakin (DSP), actin B (ACTB), eukariotic translational elongation factor 1 alpha 1 (EEF1A1), GDP dissociation inhibitor 2 (GDI2), gelsolin (GSN), histone H2B type 1-K (HISTH2BK), histone H3.1 (HIST1H3), histone H4 (HIST1H4), heat shock protein B 1 (HSPB1), lactic dehydrtogenase A (LDHA), galectin 3 (LGALS3), galectin 7 (LGALS7), POF1B actin binding protein (POF1B), S100 calcium binding protein A7 (S100A7), S100 calcium binding protein A8 (S100A8), S100 calcium binding protein A9 (S100A9), serpin family B member 3 (SERPINB3), stratifin (SFN), small prolin rich protein 1 A (SPRR1A), small proline rich protein 2 D (SPRR2D), tubulin alpha 1 B chain (TUB1AB) and ALMS1 centrosome and basal body associated protein (ALMS1) in the skin sample is determined. The expression level is compared to the same one or more proteins from a control sample wherein a statistically different expression level of the one or more proteins from the subject's skin sample as compared to the expression level of the same one or more proteins from the control sample identifies the subject as being at risk of the subject as being at risk of developing a food allergy. In yet another aspect, the expression levels are increased about a two-fold to about a three-fold (or about a 200% to 300% increase) as compared to the control levels. In one aspect, the control sample is from one or more subjects having atopic dermatitis without having a food allergy.

A further aspect of the invention comprises determining the ratio of esterified ω-hydroxy fatty acid sphingosine ceramides (EOS CER) to nonhydroxy fatty acid sphingosine ceramides (NS CER) in the skin sample from the subject. The ratio from the skin sample is then compared to the ratio of EOS CER to NS CER from a control sample. A decreased ratio in the skin sample as compared to the control sample further identifies the subject as being at risk of developing a food allergy.

In one aspect of the invention, the subject is human. In, one aspect, the subject is a child (less than 18 years of age). In another aspect, the subject is an infant. Infant as used herein is defined as up to two years (24 months) of age. In addition, an asymptomatic subject, is a subject that is not producing or showing symptoms of an allergic disease. For example, an AD asymptomatic subject is a subject that is not producing or showing symptoms of AD such as, itching, red patches on the skin (especially on the hands, feet, ankles, wrists, neck, upper chest, eyelids, inside the bend of the elbows and knees, face and scalp); small, raised bumps which can leak fluid and crust over when scratched; thickened, cracked, dry, scaly skin; and raw, sensitive, swollen skin from scratching. Most often, AD begins before age 5 and may persist into adolescence and adulthood. For some AD subjects, it flares up periodically and then clears up for a time.

In one aspect, once an asymptomatic subject is diagnosed as having an allergic disease, treatment can commence immediately to reduce the severity and/or delay the onset of symptoms.

The term "sample" or "patient sample" or "subject sample" or "test sample" can be used generally to refer to a sample of any type which contains products that are to be evaluated by the present methods, including but not limited to, a skin sample including a skin epidermal sample, a skin sample from the *Stratum corneum*, a tissue sample and/or a bodily fluid sample. The *Stratum corneum* is the outer layer of the skin (epidermis). It serves as the primary barrier between the body and the environment. The *Stratum corneum* (SC) is multi layered and is composed of dead, anucleated, flattened corneocytes. The *Stratum corneum* has a thickness between 10 and 40 μm and can contain about 15-20 layers. In one aspect of the invention, the skin sample comprises skin layers 1, 2, and/or the sum of layers 1 and 2 from the SC. In yet another aspect of the invention, the skin sample comprises skin layers 3, 4, and/or the sum of layers 3 and 4 from the SC. In still another aspect, the skin sample comprises layers 15, 16 and/or the sum of layers 15 and 16 from the SC. In one aspect, the skin sample is taken from non-lesional skin (i.e., skin that appears healthy or normal looking, without any rash). In yet another aspect. The skin sample is taken from lesional skin.

The control sample can be obtained from one or more one or more non-atopic (NA) subjects (subjects that do not have a history of atopic dermatitis), and/or from one or more subjects having atopic dermatitis without having a food allergy.

The cells in the skin sample for example are not necessarily of the same type, although purification methods can be used to enrich for the type of cells that are preferably evaluated. Cells can be obtained, for example, by a tape stripping method (also referred to as "skin taping"), scraping of a tissue, and processing of a tissue sample to release individual cells. In one aspect, an adhesive tape is applied to a target area of the skin of the subject in a manner sufficient to isolate an epidermal sample adhering to the adhesive tape. In one aspect, the epidermal sample comprises cells from the *Stratum corneum* of the subject. In one aspect, the tape comprises a rubber adhesive. In regards to removal or extraction of cells and thus lipids from the skin sample, the skin material can be removed from tape strips by scraping it out manually by a rubber scraper, a scraper comprising thermoplastic elastomer material, or using an automated tool with rubber or Teflon scraper of any form, in an alcohol solvent (such as 1-30%). The alcohol can be methanol, ethanol, butanol or isopropanol. Alternatively, the tape strip material can be removed from the tape stripes by sonication in an alcohol solution as noted above. Alternatively, skin lipids, proteins, and/or filaggrin breakdown products can be directly extracted from tape strips by supercritical extraction. In one aspect of the invention, the skin sample can be taken from one or more regions of the subject's body, including lesional and/or non-lesional skin. In one aspect, 4 or fewer skin tapes are applied to the subject to obtain the subject's sample. In yet another aspect, one or more skin samples can be obtained and the expression level of one or more proteins disclosed herein, and/or the levels of filaggrin breakdown products disclosed herein, and/or the lipids disclosed herein, can be analyzed by the methods provided herein.

Methods to measure protein expression levels generally include, but are not limited to: mass spectrometry, Western blot, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, fluorescence activated cell sorting (FACS), U-PLEX® Biomarker Group 1 (Human) Multiplex Assays (Meso Scale Discovery (MSD), and flow cytometry, as well as assays based on a property of the protein including but not limited to enzymatic activity or interaction with other protein partners. Binding assays are also well known in the art. For example, a BIAcore machine can be used to determine the binding constant of a complex between two proteins. The dissociation constant for the complex can be determined by monitoring changes in the refractive index with respect to time as buffer is passed over the chip (O'Shannessy et al., 1993, *Anal. Biochem.* 212:457; Schuster et al., 1993, *Nature* 365:343). Other suitable assays for measuring the binding of one protein to another include, for example, immunoassays such as enzyme linked immunoabsorbent assays (ELISA) and radioimmunoassays (RIA); or determination of binding by monitoring the change in the spectroscopic or optical properties of the proteins through fluorescence, UV absorption, circular dichroism, or nuclear magnetic resonance (NMR). An example of a method to determine the level of filaggrin breakdown products can be liquid chromatography electrospray ionization tandem mass spectrometry (LC-ESI-MS/MS).

As used herein, an elevated (or increased) level (such a protein expression level) means that the level is statistically higher in comparison to the same levels (such as the same proteins) from control subjects. An increase level is about a 2-fold, 2.1-fold, 2.2-fold, 2.3-fold, 2.4-fold, 2.5-fold, 2.6-fold, 2.7-fold, 2.8-fold, 2.9-fold or about 3-fold increase (or about a 200% to 300% increase) as compared to control levels. A decreased level means that the level is statistically lower in comparison to the same levels from control subjects. A decrease level is about a 1.5-fold, 1.6-fold, 1.7-fold, 1.8-fold, 1.9-fold, 2.0-fold, 2.1-fold, 2.2-fold, 2.3-fold, 2.4-fold, 2.5-fold, 2.6-fold, 2.7-fold, 2.8-fold, 2.9-fold or about a 3-fold decrease (or about a 150%-300% decrease) as compared to control levels.

In some aspects of the invention, the subjects can be treated by administration of a pharmaceutical composition comprising one or more compounds including but not limited, corticosteroids, leukotriene antagonists, anti-cytokine antibodies, anti-cytokine receptor antibodies, anti-IgE antibody, anti-interleukin 14 (IL14) antibodies, anti-interleukin 13 (IL13) antibodies, JAK kinase inhibitors, JAK/STAT inhibitors, antibiotics, a phosphodiesterase inhibitor, a cream comprising filaggrin or components thereof, ceramide rich emollients, and combinations thereof. In one aspect, the underlying skin inflammation in the subject, causing the skin barrier abnormalities is treated with the compound. In some aspects of the invention, the pharmaceutical composition is administered by an administration route such as local administration, topical administration, and/or injection.

In some aspects of the invention, the subject has or is at risk of having a food allergy. In one aspect, the food allergy is a peanut allergy, a milk allergy, an egg allergy, a wheat allergy, a tree nut allergy and/or a combination thereof.

The following examples are provided for illustrative purposes, and are not intended to limit the scope of the invention as claimed herein. Any variations which occur to the skilled artisan are intended to fall within the scope of the present invention. All references cited in the present application are incorporated by reference herein to the extent that there is no inconsistency with the present disclosure.

Examples

Materials and Methods
Study Participants

A total of 75 children between 4 and 17 years of age were enrolled. The AD participants had active skin disease without a history of eczema herpeticum diagnosed using published criteria (Beck L A, Boguniewicz M, Hata T, et al. Phenotype of atopic dermatitis subjects with a history of eczema herpeticum. J Allergy Clin Immunol 2009; 124:260-9, 9 e1-7) and were stratified into 2 groups based on their food allergy status: 1) 21 AD FA+ with food allergy to peanut. The following criteria were used for diagnosis of peanut allergy: peanut skin prick test wheal ≥8 mm which has been reported to significantly correlate with immediate clinical reactions to oral peanut challenge (Roberts G, Lack G. Diagnosing peanut allergy with skin prick and specific IgE testing. J Allergy Clin Immunol 2005; 115:1291-6) as well as documentation of a previous positive oral food challenge to peanut or convincing history of an immediate allergic reaction to peanut. 2) 19 AD FA− children with no FA. These participants had no personal history of FA (based on ability to ingest foods without adverse reactions) as well as a negative skin prick test (wheal<3 mm) to peanut, milk, egg, wheat, soy, shellfish mix (clam, crab, oyster, scallops and shrimp), almond, english walnut, hazelnut, cashew, brazil nut, and sesame seed. A third comparison group consisted of 22 NA controls defined as those without a personal history of atopic diseases and negative skin prick tests to common foods and aeroallergens. Group four included pediatric patients with FA to peanut with no history of AD (FA only). The four diagnostic groups (AD FA+, AD FA−, FA only and NA) were balanced for age, gender, and race, and the two AD groups had similar skin disease severity (Table 1). Blood samples were taken and serum total IgE (kilounits per liter) and IgE to peanut, egg, and milk measurements were determined using the ImmunoCAP250-Thermofisher Scientific/Phadia.

TABLE 1

Characteristics of study participants by diagnostic group*

| | AD FA+<br>N = 21 | AD FA−<br>N = 19 | NA<br>N = 22 | FA only<br>N = 13 | p-value |
|---|---|---|---|---|---|
| Demographics | | | | | |
| Gender: | | | | | |
| Female | 9 (42.9%) | 10 (52.6%) | 11 (50.0%) | 3 (23.1%) | 0.81 |
| Male | 12 (57.1%) | 9 (47.4%) | 11 (50.0%) | 10 (76.9%) | |
| Race: | | | | | |
| White | 17 (81.0%) | 15 (78.9%) | 18 (81.8%) | 13 (100%) | 0.94 |
| African-American | 4 (19.0%) | 3 (15.8%) | 4 (18.2%) | 0 (0.00%) | |
| Other | 0 (0.00%) | 1 (5.26%) | 0 (0.00%) | 0 (0.00%) | |
| Age (yrs.) | 10.8 [8.04; 13.3] | 11.5 [10.3; 15.3] | 9.51 [7.65; 14.3] | 10.0 [6.0; 14.0] | 0.37 |
| Age Group: | | | | | |
| <12 yrs. | 12 (57.1%) | 11 (57.9%) | 13 (59.1%) | 8 (61.5%) | 0.99 |
| ≥12 yrs. | 9 (42.9%) | 8 (42.1%) | 9 (40.9%) | 5 ((39.5%) | |
| Clinical | | | | | |
| Eczema Area and Severity Index (EASI) | 11.2 [8.80; 22.5] | 8.20 [4.60; 16.7] | | | 0.13 |
| Nottingham Eczema Severity Score (NESS) | 11.0 [9.00; 11.0] | 11.0 [9.50; 12.0] | | | 0.46 |
| SCORing Atopic Dermatitis (SCORAD) | 43.1 [35.1; 55.4] | 37.4 [28.4; 50.3] | | | 0.26 |
| SCORAD: | | | | | |
| Mild (<20) | 1 (4.76%) | 2 (10.5%) | | | 0.71 |
| Moderate (20-40) | 8 (38.1%) | 8 (42.1%) | | | |
| Severe (>40) | 12 (57.1%) | 9 (47.4%) | | | |
| Pruritus scale (SCORAD) | 5.80 [4.90; 7.00] | 4.40 [2.90; 5.95] | | | 0.15 |
| Peanut IgE (kU/L) | 13.8 [4.22; 50.2] | 0.07 [0.07; 0.12] | | | <0.001 |
| Peanut Wheal Size (mm): | 16.5 [15.0; 23.0] | 0.0 [0.0; 0.0] | | >8 | <0.001 |
| Egg Wheal Size ≥3 mm | 12 (57.1%) | 0 (0.0%) | | | <0.001 |
| Milk Wheal Size ≥3 mm | 6 (28.6%) | 0 (0.0%) | | | <0.001 |
| # Positive (≥3 mm) Skin Tests Foods** | 5.0 [3.0; 7.0] | 0.0 [0.0; 0.0] | | | <0.001 |

*Medians [1st, 3rd quartile] are used for continuous variables and numbers (percents) for categorical variables. P-values for comparisons between diagnostic groups were calculated with the use of the Kruskal-Wallis test by ranks for continuous variables and the chi-square test for categorical variables.
**There was a total of 12 food skin prick tests: peanut, milk, egg, wheat, soy, shellfish mix (clam, crab, oyster, scallops and shrimp), almond, english walnut, hazelnut, cashew, brazil nut, sesame seed.

Key exclusion criteria included: skin disease other than AD that may affect skin barrier function; known or suspected immunosuppression; history of serious life-threatening reaction to latex, tape, or adhesives; pregnant or lactating females; and clinically active viral or bacterial skin infections. All participants avoided any treatments, baths, and skin creams or emollients which may potentially affect skin microbiome or skin barrier function before sample collection.

Skin Tape Strip (STS) Collection

D-SQUAME® tape strips (22 mm diameter, CuDerm, Dallas, TX) were collected from the upper extremities. Thirty non-lesional and 20 lesional (AD participants) STS were collected for proteomics/lipidomics. Non-lesional STS were collected adjacent to the corresponding lesional sampling site. The D-SQUAME® pressure instrument D500 was used to apply all tape strips with equivalent pressure (e.g. 225 g/cm$^2$).

On application of the first tape disc, 4 marks were placed around the disc with a pen so that subsequent discs could be applied to the same location. Each tape disc was placed adhesive side up in a separate well of a 12-well plate. Plates were kept on dry ice during the tape strip collection. STS for proteomics/lipidomics were frozen without processing further.

Skin Disease Severity Assessments

AD severity was evaluated using the SCORing Atopic Dermatitis (SCORAD) (Severity scoring of atopic dermatitis: the SCORAD index. Consensus Report of the European Task Force on Atopic Dermatitis. Dermatology 1993; 186: 23-31), which includes a visual analog scale (VAS), the Nottingham Eczema Severity Score (NESS) (Emerson R M, Charman C R, Williams H C. The Nottingham Eczema Severity Score: preliminary refinement of the Rajka and Langeland grading. Br J Dermatol 2000; 142:288-97; Phan N Q, Blome C, Fritz F, et al. Assessment of pruritus intensity: prospective study on validity and reliability of the visual analogue scale, numerical rating scale and verbal rating scale in 471 patients with chronic pruritus. Acta Derm Venereol 2012; 92:502-7), and the Eczema Area and Severity Index (EAST) (Leshe Y A. What the Eczema Area and Severity Index score tells us about the severity of atopic dermatitis: An interpretability study. Br J Dermatol 2015; 172:1353-7) (Table 1). Enrollment of AD FA+ and AD FA− participants was balanced based on AD severity (mild, moderate, severe) as determined by the NESS.

Filaggrin Skin Level Assessment

Filaggrin breakdown products, cis/trans-urocanic acid (total UCA) and pyrrolidone carboxylic acid (PCA), also known as pyroglutamic acid, were quantified via a liquid chromatography electrospray ionization tandem mass spectrometry (LC-ESI-MS/MS) approach on a Sciex 6500QTRAP mass spectrometer coupled with a Shimadzu Nexera X2 UHPLC system (Leung D Y M, Calatroni A, Zaramela L S, et al. The nonlesional skin surface distinguishes atopic dermatitis with food allergy as a unique endotype. Sci Transl Med. 2019; 11(480). pii: eaav2685 essentially as described in Joo K M, Han J Y, Son E D, et al. Rapid, simultaneous and nanomolar determination of pyroglutamic acid and cis-/trans-urocanic acid in human Stratum corneum by hydrophilic interaction liquid chromatography (HILIC)-electrospray ionization tandem mass spectrometry. J Chromatogr B Analyt Technol Biomed Life Sci 2012; 897:55-63; but with modification which allows simultaneous quantitative analysis of FLG breakdown products and skin lipids. Briefly, Stratum corneum from STS #1-2, STS #3-4, STS #5-6, as well as STS #15-16, was removed by scraping STS in 2 ml water-methanol (9:1, v/v) solution in a Petri dish with a rubber cell scraper. Floating Stratum corneum particles were carefully transferred into 8 ml glass screw cap tubes and Petri dishes were washed twice with 1 ml alcohol that was combined with the first water alcohol portion then subjected to a modified Bligh and Dyer extraction (Bligh E G, Dyer W J. A rapid method of total lipid extraction and purification. Can J Biochem Physiol 1959; 37:911-7). A known amount of U-[$^{13}$C, $^{15}$N]proline was added at this step to ensure absolute quantitation of targeted molecules. Extraction was performed overnight by adding 0.5 ml alcohol and 0.4 ml chloroform, then phase separation was achieved by adding 2.2 ml chloroform and 0.63 ml 2% formic acid, intensive vortexing, and centrifugation (2,000 g×10 min). After centrifugation, the upper water-alcohol phase was carefully collected, then evaporated under a nitrogen stream, redissolved in acetonitrile/water (1:1) and subjected to the LC-MS/MS analysis. The chloroform layer was collected for lipid analyses. The protein interface was subjected to hydrolysis with 1N NaOH for 3 hours at 80° C. then neutralized with 1N HCl, and sample protein content was measured using a DC Protein Assay kit (Bio-Rad, Hercules, CA) and bovine serum albumin (BSA) as a protein standard.

LC separation of cis/trans-UCA, PCA, and praline was achieved using an Acquity UPLC BEH Amide (2.1×100 µm, 1.7 µm particle size) column using a gradient from acetonitrile (Solvent A) to methanol:water:formic acid (65:35:0.5, with 5 mM ammonium formate) (Solvent B) and the following elution program: hold at 5% B until 0.5 min then linear increase to 20% B at 1 min then increase to 60% B at 3 min, hold at 60% B until 4.1 min then decrease to 5% B by 4.5 min and hold at 5% B until 5 min. All amino acids were detected in positive ions mode using the following transitions: mass to charge (m/z)139.1>m/z 121.1 (UCA), m/z 130.2>m/z 83.9 (PCA), and m/z 122.1>m/z 75.0 (U-[$^{13}$C, $^{15}$N]proline). Exact quantitation of PCA and cis/trans-UCA was achieved by creating standard curves of variable amounts of analytes versus a fixed amount of the internal standard (U-[$^{13}$C, $^{15}$N]proline).

Analysis of Stratum Corneum Lipids

Skin Tape Strip Processing for Lipid Extraction.

The bottom chloroform layer collected during skin tape extraction for filaggrin skin level assessment was used for lipid analysis by mass spectrometry. A fixed amount of the internal standard (N-palmitoyl-D-erythro-sphingosine (d7), D7-ceramide) was added at the beginning of the extraction process. Data were normalized to the total amount of hydrolyzed protein determined as described above.

Lipid Analysis by Targeted Lipid Chromatography Tandem Mass Spectrometry.

EOS CER, which are exceptionally long-chain ceramides required for normal skin barrier, and NS CER were identified and quantified using a targeted LC-ESI-MS/MS approach on a Sciex 6500QTRAP mass spectrometer coupled with a Shimadzu Nexera X2 UHPLC system as previously described.[21] All molecules were detected in positive ions mode. EOS CER and NS CER were detected as a transition from molecular ions to the m/z 264, m/z 292, and m/z 320 as the inventor's work has identified all three sphingoid bases (C18-, C20-, and C22-sphingosine) being present in human skin ceramides. Chromatography was performed on an Ascentis Express RP-Amide 2.7 µm 2.1×50 mm column using gradient elution from methanol:water: formic acid (65:35:0.5, 5 mM ammonium formate) to methanol:chloroform:water:formic acid (90:10:0.5:0.5, 5 mM ammonium formate). Absolute amounts of NS CER were determined in a quantitative and semi-quantitative way by using correction factors from standard curves created using variable amounts of N-14:0-24:0 ceramides with C18-sphingosine as a base versus a fixed amount of D7-ceramide (all from Avanti Polar Lipids, Alabaster, AL). Correction factors for molecular species for which there are no available standards were used with best possible approximation to the closest available molecular species of ceramide standards. Absolute amounts of EOS CER were determined in a semi-quantitative way by using a correction factor from a standard curve created using variable amounts of N-24:0-D-erythrosphingosine (24:0-CER) versus D7-ceramide.

Proteomic Analysis

Materials.

Mass spectrometry grade acetonitrile and formic acid were obtained from Thermo Fisher Scientific. Deionized water was obtained from a Millipore Milli-Q filtration system. Triethylammonium bicarbonate (TEAB), iodoacetamide (IAA), dithiothreitol (DTT), acetone, trichloroacetic acid (TCA), and triflouroethanol (TFE) were obtained from Sigma-Aldrich; Trypsin/Lys-C mix from Promega and labeled with tandem mass tag (TMT) 10-plex reagents from Thermo.

During liquid chromatography-mass spectrometry (LC-MS) analysis, peptides were loaded on to a 75 µm internal diameter 10 cm long trapping column (Molex) containing 10 µm diameter C18 beads (YNC) and chromatographically separated on a 75 µm internal diameter 40 cm column with an integrated nanospray emitter from New Objective packed with Dr. Masich Repro-SIL 3 µm diameter C-18 beads. LC-MS analysis was carried out with a nanoEasy-LC 1200 pump (Thermo) and an Orbitrap Lumos (Thermo).

Sample Preparation.

For each sample, protein content was extracted from 15 STS (every other tape down to tape 30) with 50 mM ammonium bicarbonate, 1% SDS buffer supplemented with HALT protease inhibitors and 10 mM DTT. SDS was removed using a detergent removal spin column, protein concentrations were determined, and 50 µg of protein were used for proteomic analysis.

Each sample was reduced in 5 mM DTT for 1 hour at 56° C., and alkylated in 10 mM IAA, in the dark, at room temperature for 30 minutes. The protein content was precipitated with cold (−20° C.) 10% w/v TCA in acetone. After centrifugation at 16,000×g for 15 minutes, the supernatant was discarded, and the pellet was washed with cold acetone. The dried protein pellet was dissolved in 100 µL of 5% TFE 100 mM TEAB and digested with 3 µg of Trypsin Lys-C mix overnight at 37 C. A 20 µL aliquot of each sample (10 µg of protein) was labeled with 0.5 mg of TMT 10-plex reagents for 2 hours at room temperature. The TMT labeled samples were combined into sets containing 3 samples from each group. Each TMT set was step-fractionated on an Oasis plate (Waters) using 7 mM TEAB (pH ~8) in 5, 10, 25, and 70% acetonitrile. Each fraction was lyophilized and stored at −20 C. Immediately prior to LC-MS analysis, the fractionated samples were reconstituted in 100 µL of 0.1% formic acid, 2% acetonitrile.

Sample Analysis.

Five microliters of each fraction were separated over a binary reversed phase gradient using aqueous 2% acetonitrile 0.1% formic acid (mobile phase A), and 0.1% formic acid in 90% acetonitrile (mobile phase B). Samples were loaded in 0% B, B was increased to 6% at the start of the gradient, followed by a linear ramp to 32% over 90 minutes, a linear ramp to 40% over 10 minutes, a ramp to 95% B over 10 minutes, and held at 95% B for 10 minutes (120 minute total).

During MS analysis, precursor ion scans spanning 400-1600 m/z were acquired at 120000 (m/z=200) resolution every 3 seconds. Detected ions in the +2 to +6 charge states were individually isolated by the quadrupole in 0.4 m/z bins and fragmented in order of highest intensity by high energy collisional dissociation (38 normalized collision energy). Fragment ion scans were acquired at 50000 resolution (at m/z=200) after accumulation to an automatic gain control of 50000 for a maximum of 86 ms. Fragmented ions were excluded from redundant fragmentation for 15 seconds.

Data Analysis.

The LC-MS data were searched against the SwissProt Homo Sapien database (July 2018; 20,368 sequences) with MASCOT 2.6.2 and Percolator re-scoring followed by quantitative analysis in Proteome Discoverer 2.2 (Thermo). Carbamidomethylation of cysteine and TMT conjugation of lysines and peptide N-termini were set as static modifications. Deamidation of asparagine and glutamine and oxidation of methionine were set as variable modifications and up to 2 tryptic missed cleavages were allowed. Spectra were matched to theoretical tryptic peptides using 5 parts-per-million (ppm) precursor and 0.01 Da fragment mass error tolerances and filtered to 1% false discovery rate (FDR).

For quantitation, the identified spectra were filtered to exclude chimeric spectra with greater than 30% co-isolation interference, and peptides with deamidation or oxidation. Peptides were quantified based on the reporter ion signal to noise values. Each channel was adjusted for loading by leveling the summed peptide abundance to the channel with the highest summed peptide intensity. Proteins were quantified using only unique peptides, and the average protein abundance across all samples was scaled to 100. Fold changes and (analysis of variance) ANOVA significance values were calculated based on the scaled protein abundances.

Results

Participant Characteristics

A total of 75 participants were enrolled (AD FA+, n=21; AD FA−, n=19; NA, n=22; FA only n=13). Table 1 displays demographics, disease severity, and food allergy assessment. The 0.3 diagnostic groups were balanced for age, gender, and race. Furthermore, the 2 AD groups had similar skin disease severity as measured by SCORing Atopic Dermatitis (SCORAD), the Nottingham Eczema Severity Score (NESS), and the Eczema Area and Severity Index (EASI). The proportion of mild, moderate, and severe AD categorized by SCORAD was similar in the AD FA+vs AD FA− group. Four Caucasians in the AD FA+ group had FLG mutations, and none were found in the AD FA− group (data not shown). Participants in the AD FA+ group all had immediate clinical reactions to peanut and immediate skin prick wheal size to peanut of 8 mm or greater, as well as allergic sensitization to a variety of other foods (Table 1). In contrast, the AD FA− and NA groups tolerated clinical ingestion of peanut and had negative skin prick tests to peanut and other foods. Peanut-specific IgE was also significantly increased in the AD FA+ group compared to the AD FA− group (p<0.001). Patients in the FA only group had documented clinical reactions to peanut and immediate skin prick wheal size to peanut of 8 mm or greater.

Skin Filaggrin (FLG) and Lipid Content

Figure 1B:
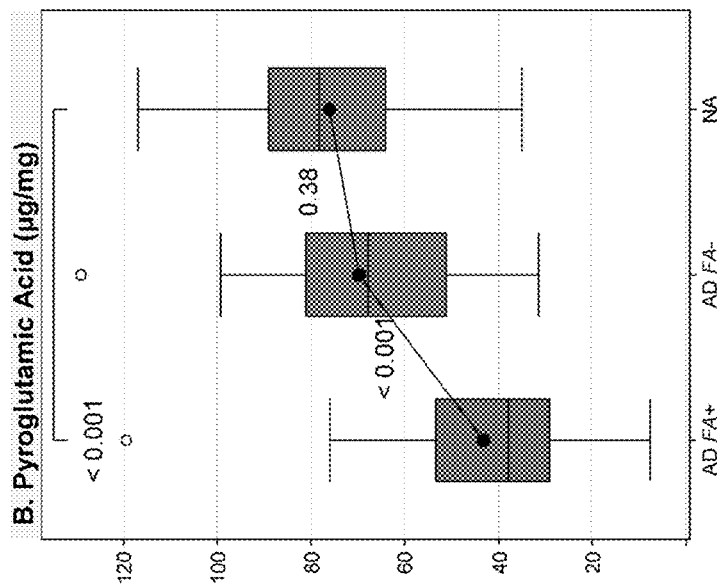

Previous studies have demonstrated a close correlation between FLG breakdown products (urocanic acid [UCA] and pyroglutamic acid [PCA]) and FLG protein levels in the skin (Kezic S. Levels of filaggrin degradation products are influenced by both filaggrin gentotype and atopic dermatitis severity. Allergy 2011; 66:934-40). Since the inflection point at STS layers 15-16 showed an upward slope in the TEWL AUC for AD FA+, the inventors focused studies of FLG breakdown products and EOS CER/NS CER on these layers. As shown in FIGS. 1A and 1B, children in the AD FA+ group had the lowest level of FLG breakdown products in the skin at non-lesional STS #15-16 among 3 of the diagnostic groups (Table 2). In AD FA−, at non-lesional STS layers #15-16, the level of FLG breakdown products was intermediate; UCA levels were significantly lower than in NA; whereas, UCA and PCA levels were significantly higher than in AD FA+(FIGS. 1A and 1B). Therefore, levels of FLU breakdown products at non-lesional skin layers #15-16 distinguished these 3 groups.

TABLE 2

Comparisons between AD groups and NA for filaggrin breakdown products

| Location | Skin Tape | Variable (μg/mg) | AD FA+ Mean (SD) | AD FA− Mean (SD) | NA Mean (SD) | AD FA+ vs AD FA− Mean Difference (95% CI), p-value | AD FA+ vs NA Mean Difference (95% CI), p-value | AD FA− vs NA Mean Difference (95% CI), p-value |
|---|---|---|---|---|---|---|---|---|
| Non-Lesional | #1-2 | Pyroglutamic Acid | 17.6 (8.2) | 27.4 (15.2) | 39.1 (16.3) | −9.9 (−20.3, 0.60), 0.014 | −21.5 (−31.6, −11.4), <0.001 | −11.6 (−22.0, −1.3), 0.024 |
| | | Total cis-trans-UCA | 8.0 (3.6) | 14.5 (10.8) | 17.7 (8.6) | −6.5 (−12.7, −0.3), 0.013 | −9.7 (−15.7, −3.7), <0.001 | −3.2 (−9.4, 2.9), 0.29 |
| | #3-4 | Pyroglutamic Acid | 69.4 (28.8) | 53.0 (25.0) | 121.2 (41.2) | 16.4 (−8.5, 41.3), 0.06 | −51.8 (−76.1, −27.5), <0.001 | −68.2 (−92.5, −43.9), <0.001 |
| | | Total cis-trans-UCA | 28.0 (12.7) | 24.3 (11.7) | 43.5 (20.6) | 3.7 (−8.3, 15.6), 0.34 | −15.6 (−27.3, −3.9), 0.006 | −19.3 (−31.0, 7.6), <0.001 |
| | #5-6 | Pyroglutamic Acid | 65.0 (34.5) | 69.7 (31.8) | 204.9 (152.7) | −4.6 (−64.8, 55.5), 0.88 | −139.8 (−197.8, −81.9), <0.001 | −135.2 (−194.7, −75.7), <0.001 |
| | | Total cis-trans-UCA | 24.2 (13.3) | 26.1 (14.4) | 42.8 (22.7) | −2.0 (−13.0, 9.1), 0.72 | −18.7 (−29.3, −8.0), <0.001 | −16.7 (−27.6, −5.7), 0.003 |
| | #15-16 | Pyroglutamic Acid | 43.3 (24.2) | 69.8 (23.8) | 76.1 (19.1) | −26.5 (−40.7, −12.3), <0.001 | −32.8 (−46.4, −19.1), <0.001 | −6.3 (−20.3, 7.8), 0.38 |
| | | Total cis-trans-UCA | 19.9 (10.8) | 30.6 (10.8) | 39.5 (11.6) | −10.7 (−17.7, −3.7), 0.004 | −19.5 (−26.3, −12.8), <0.001 | −8.9 (−15.8, −1.9), 0.013 |
| Lesional | #5-6 | Pyroglutamic Acid | 48.8 (40.5) | 40.6 (22.7) | | 8.2 (−13.1, 29.5), 0.44 | | |
| | | Total cis-trans-UCA | 16.3 (11.2) | 15.7 (10.2) | | 0.6 (−6.2, 7.5), 0.85 | | |
| | #15-16 | Pyroglutamic Acid | 40.2 (25.6) | 37.2 (20.1) | | 3.0 (−11.8, 17.9), 0.68 | | |
| | | Total cis-trans-UCA | 16.9 (11.4) | 13.7 (8.5) | | 3.1 (−3.3, 9.6), 0.33 | | |

In contrast, the levels of FLG breakdown products (UCA and PCA) at STS #5-6 in the two AD groups were similar with both showing significantly reduced levels compared to the NA group (Table 2). However, no differences in UCA and PCA levels were observed between the AD FA+ and AD FA− groups in lesional AD skin (Table 2). Importantly, the levels of FLG breakdown products in non-lesional tape strips #15-16 of the AD FA+ group were comparable to the levels seen in lesional skin samples of both AD FA+ and AD FA− participants. A strong inverse correlation was found between levels of FLG breakdown products of STS #15-16 with the corresponding TEWL assessed on non-lesional and lesional skin (Table 3).

FA+ group did separate from the AD FA− group at non-lesional STS #5-6 when comparing the EOS CER/NS CER ratio (Table 4). There was no significant difference in EOS CER levels in non-lesional skin of the AD FA− group versus NA controls at either STS #5-6 or STS #15-16. Importantly, the levels of EOS CER in non-lesional skin of AD FA+ participants were comparable to the low levels observed in lesional skin tapes #15-16 of AD FA+ and AD FA−participants. A correlation was found between levels of EOS CER with the corresponding TEWL assessed on non-lesional and lesional skin (Table 5). It is worth noting that changes in the absolute levels of EOS CER and NS CER in the AD FA+ and

TABLE 3

Correlations between filaggrin breakdown products with the corresponding TEWL

| | Non-Lesional | | Lesional | |
|---|---|---|---|---|
| Variable | Skin Tape #5-6 vs TEWL #5 | Skin Tape #15-16 vs. TEWL #15 | Skin Tape #5-6 vs TEWL Lesional | Skin Tape #15-16 vs. TEWL Lesional |
| | Pearson Correlation (95% CI), p-value | | | |
| Pyroglutamic Acid | −0.23 (−0.46, 0.02) 0.07 | −0.58 (−0.72, −0.38) <0.001 | −0.52 (−0.72, −0.25) <0.001 | −0.68 (−0.82, −0.47), <0.001 |
| Total cis-trans-UCA | −0.21 (−0.44, 0.04) 0.10 | −0.49 (−0.66, −0.28) <0.001 | −0.58 (−0.76, −0.33) <0.001 | −0.61 (−0.77, −0.37), <0.001 |

Figure 1C:
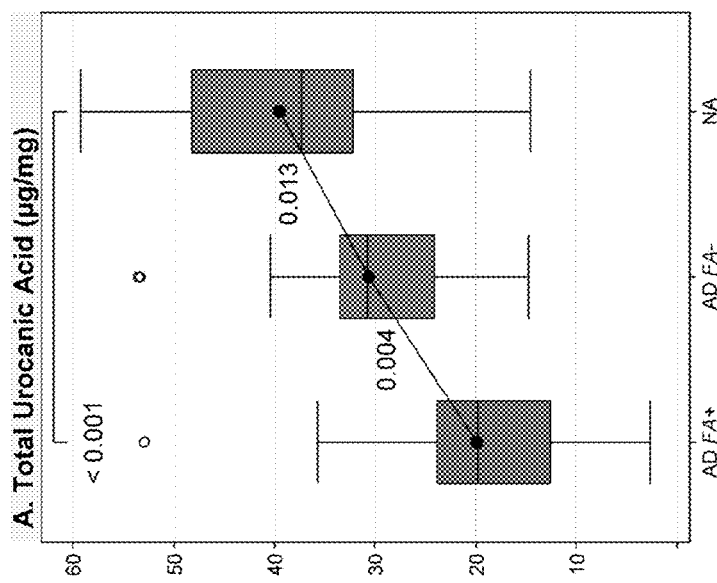
Figure 3A:
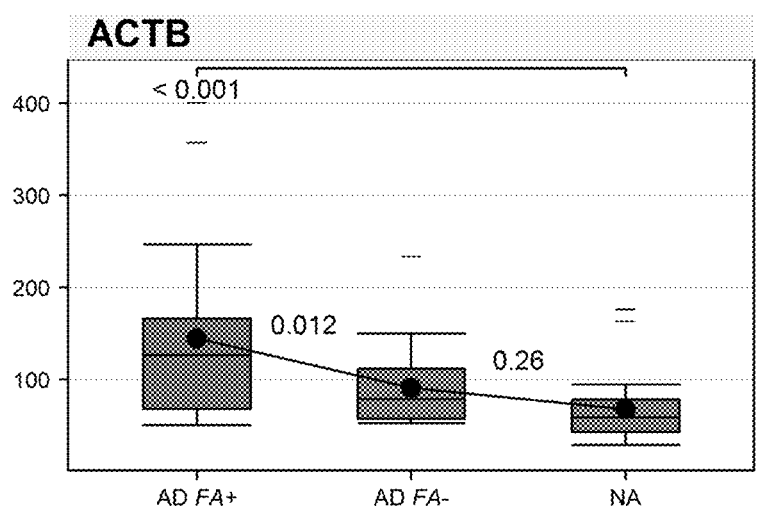
FIGS. 3A-3Z and FIG. 3AA demonstrate the expression of 27 proteins in non-lesional skin. Protein extracts were prepared from 15 skin tapes combined. Note the complete separation between AD FA+vs AD FA− and vs NA for these proteins. In the boxplots, the solid horizontal line represents the median and the filled circle represents the mean. The box margins are the interquartile range, and the whiskers extend 1.5 times the interquartile range. Observations outside the whisker are marked by a hollow circle. The annotations are the p-values from pairwise comparisons between groups.
Figure 3B:
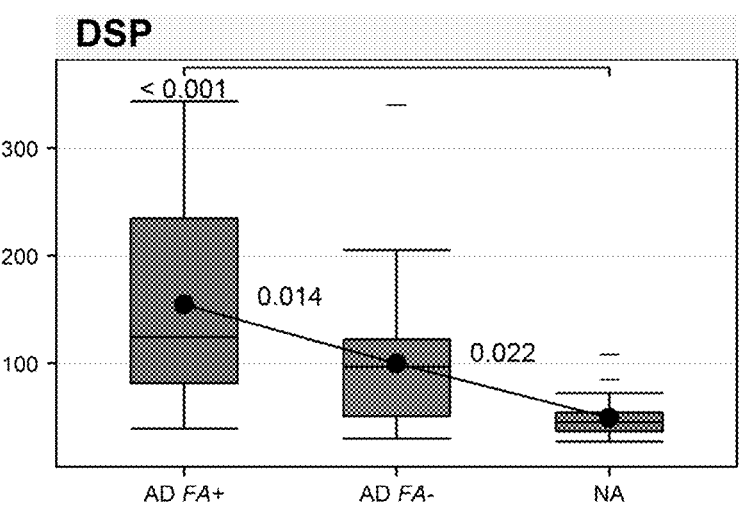
Figure 3C:
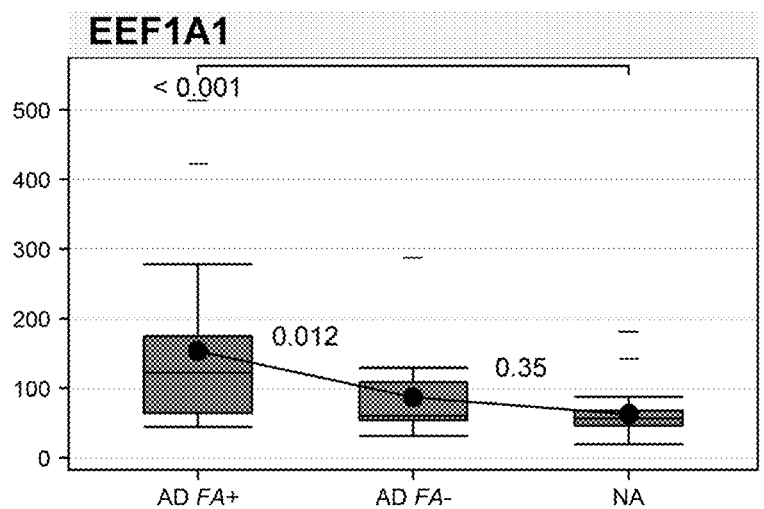
Figure 3D:
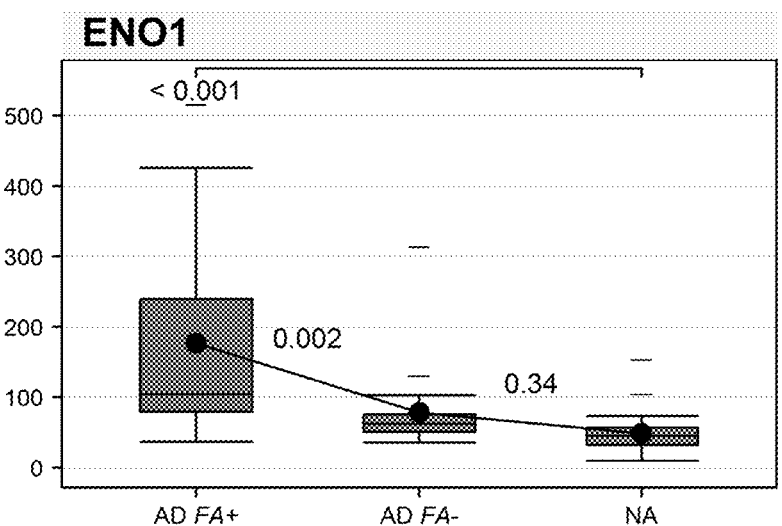
Figure 3E:
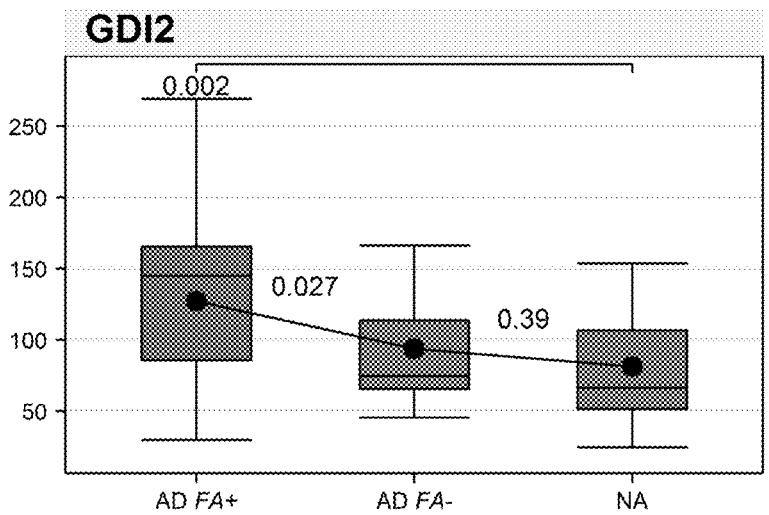
Figure 3F:
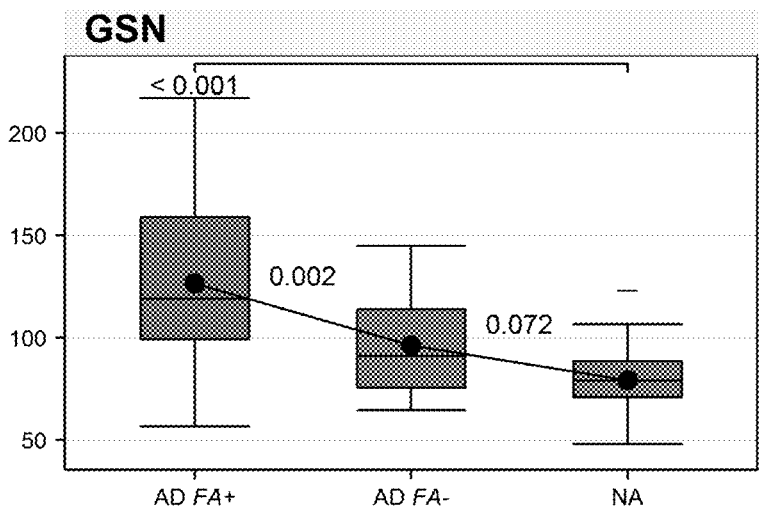
Figure 3G:
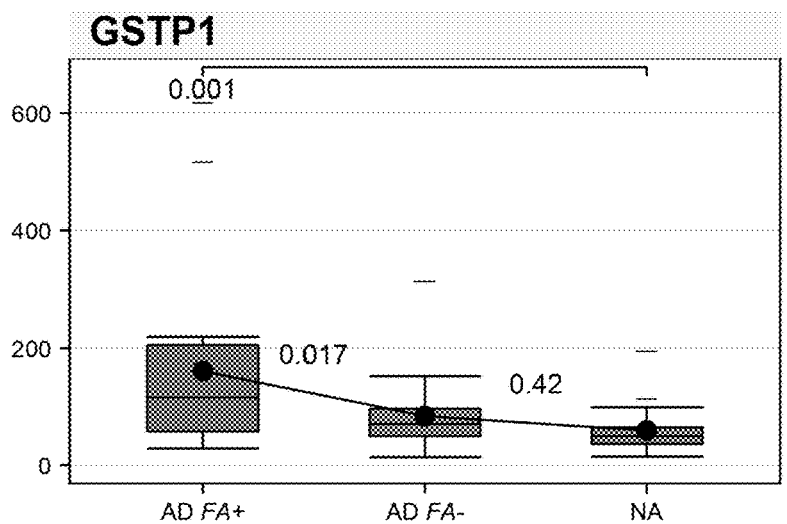
Figure 3H:
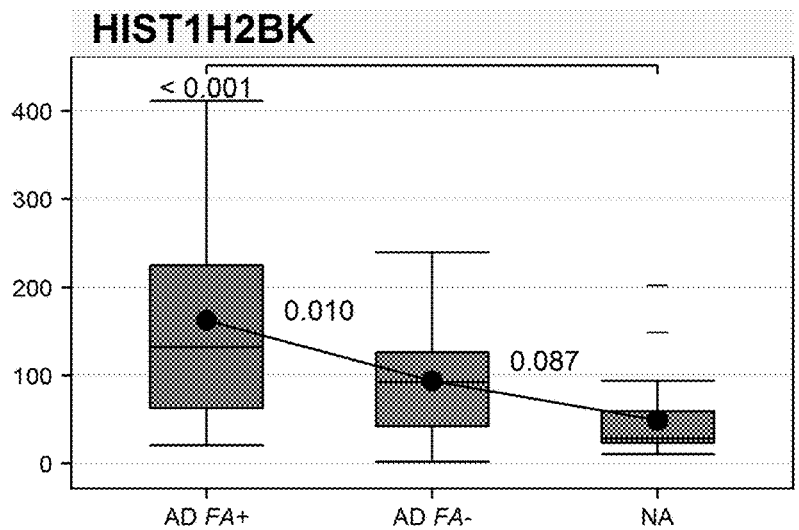
Figure 3I:
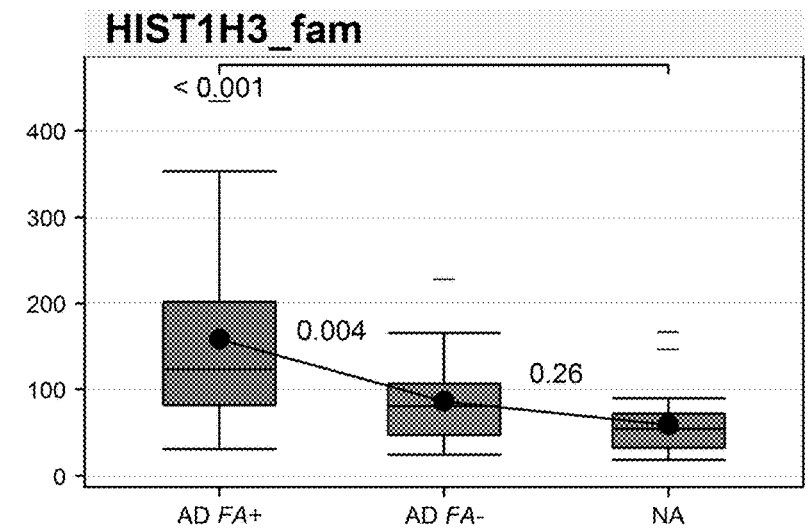
Figure 3J:
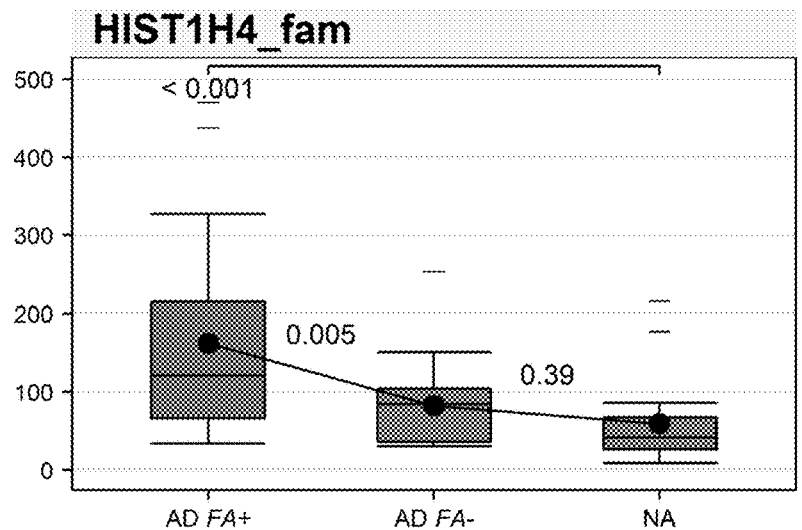
Figure 3K:
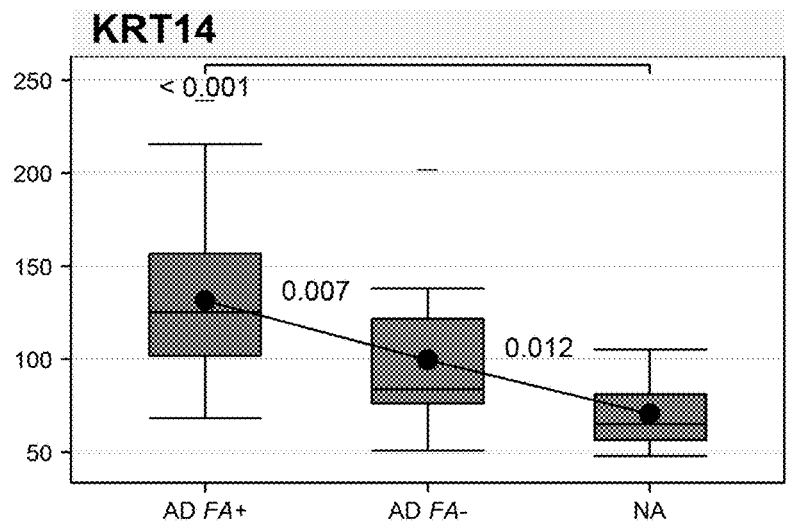
Figure 3L:
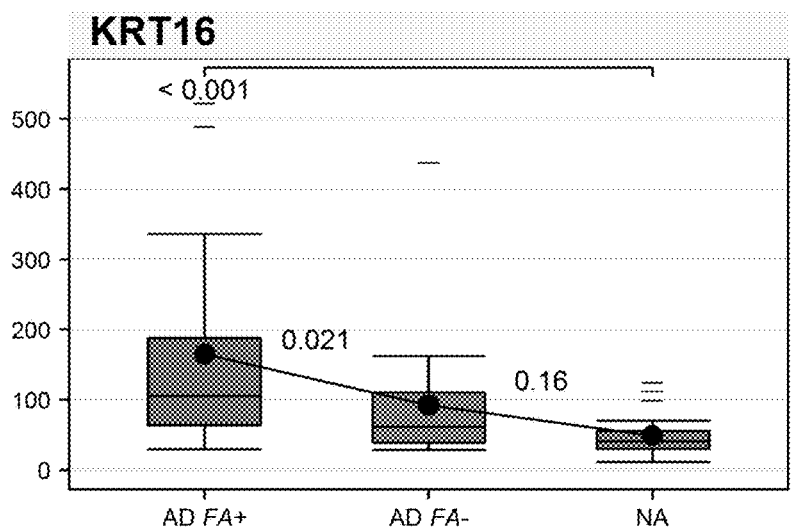
Figure 3M:
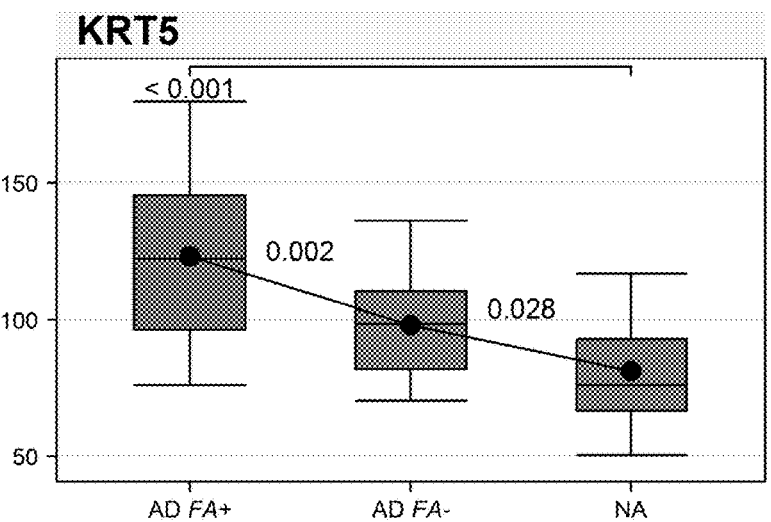
Figure 3N:
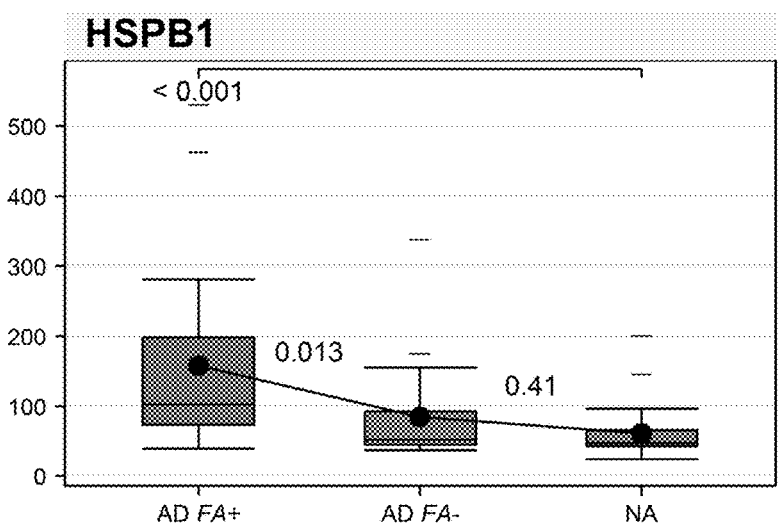
Figure 3O:
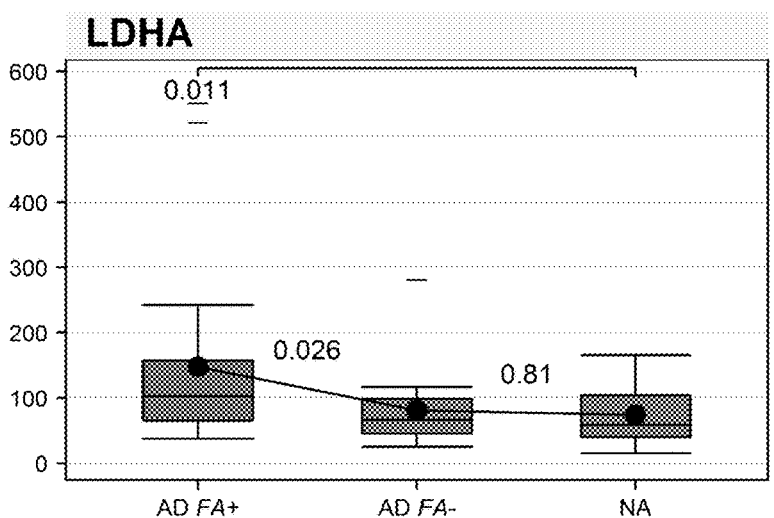
Figure 3P:
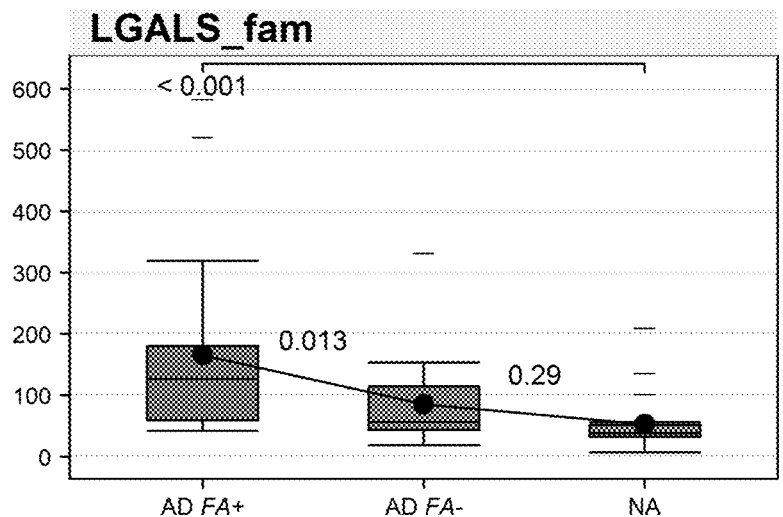
Figure 3Q:
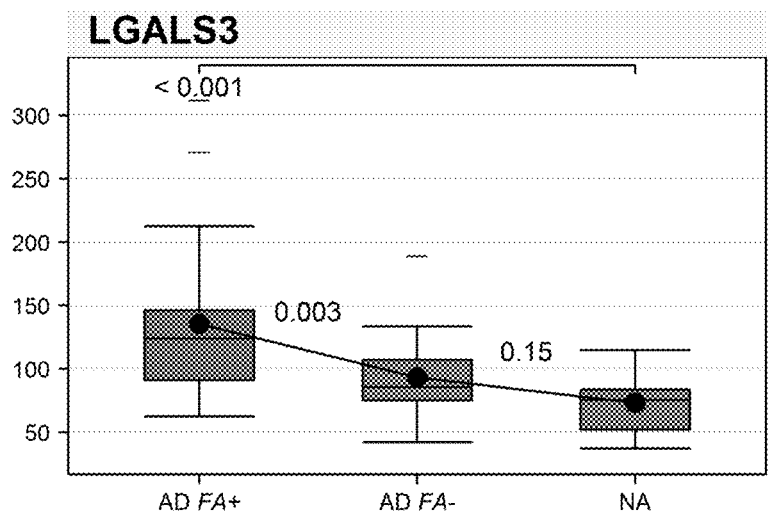
Figure 3R:
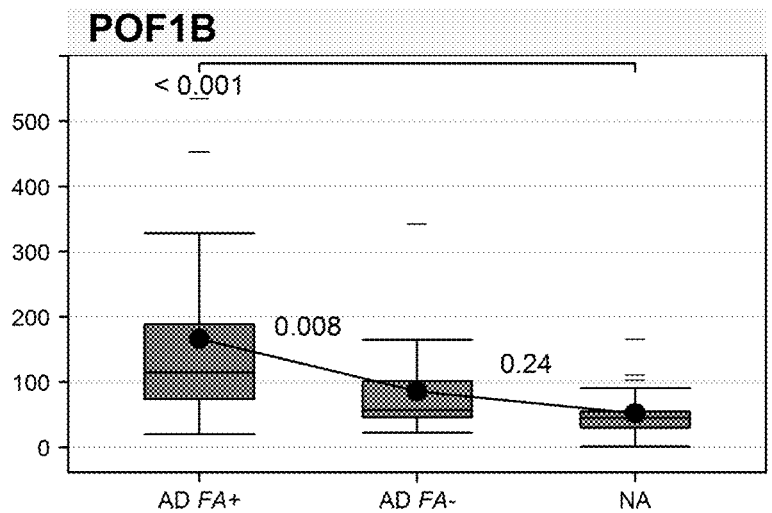
Figure 3S:
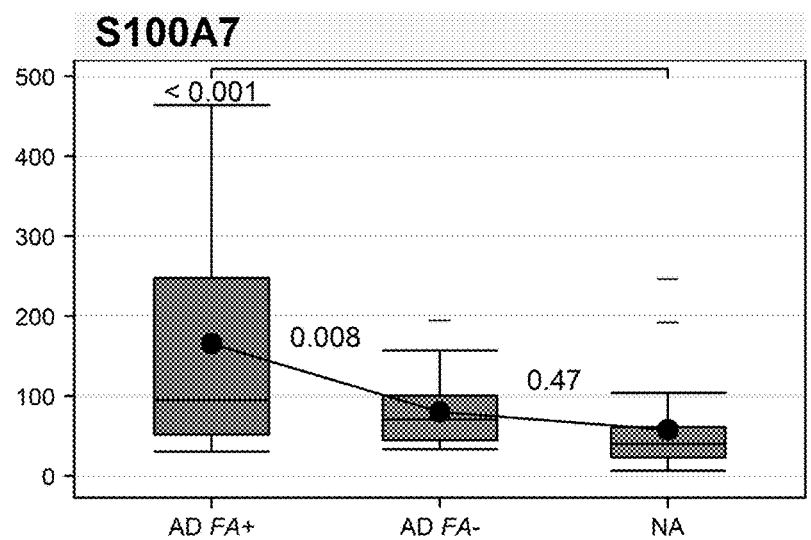
Figure 3T:
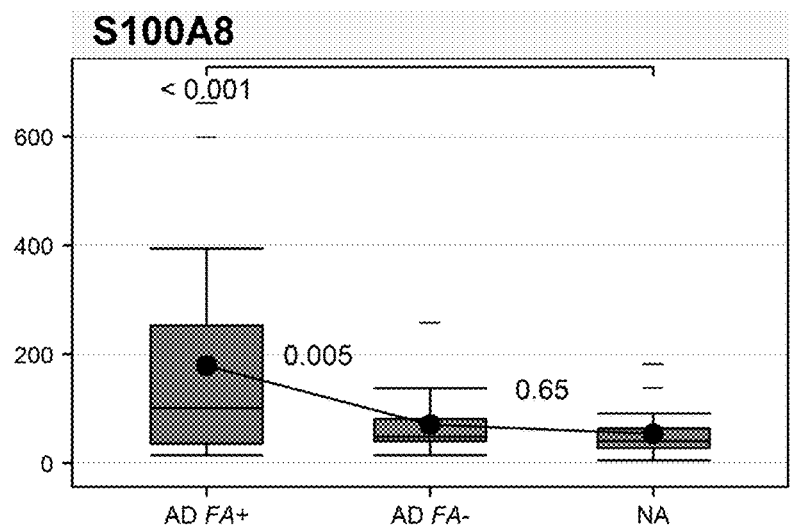
Figure 3U:
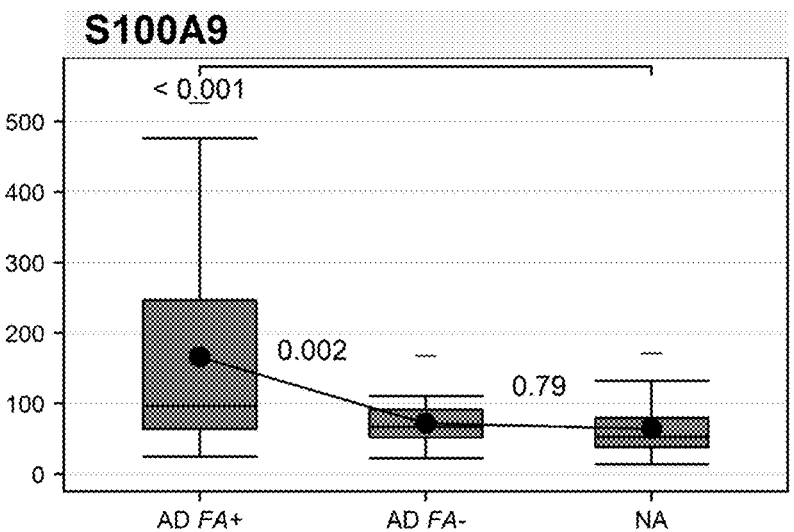
Figure 3V:
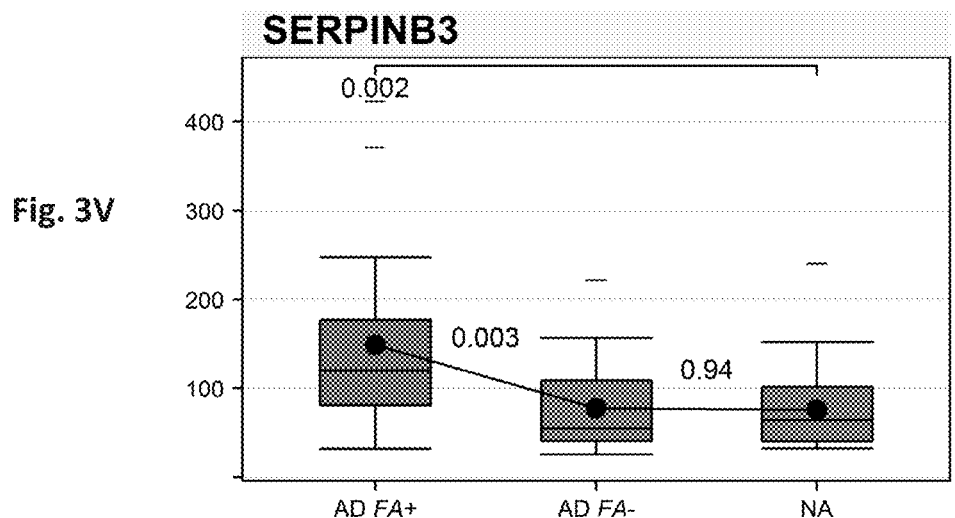
Figure 3W:
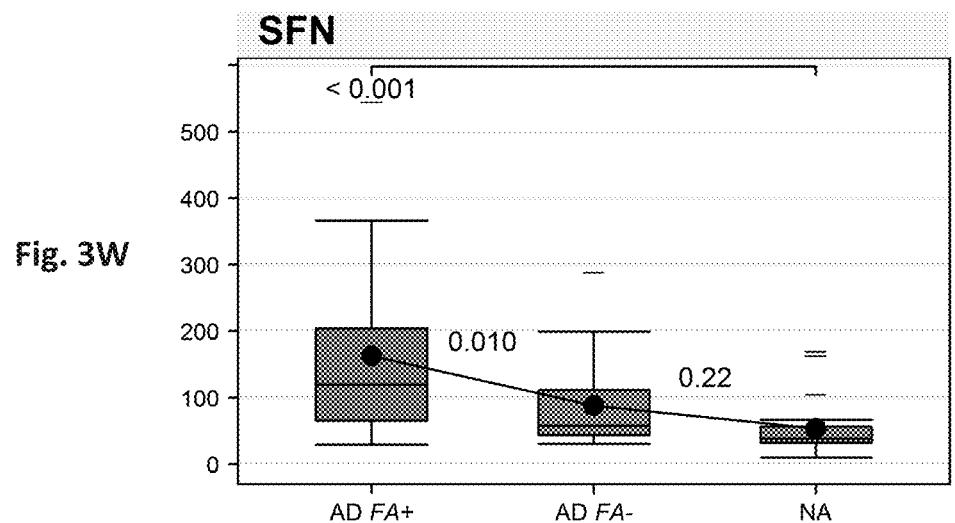
Figure 3X:
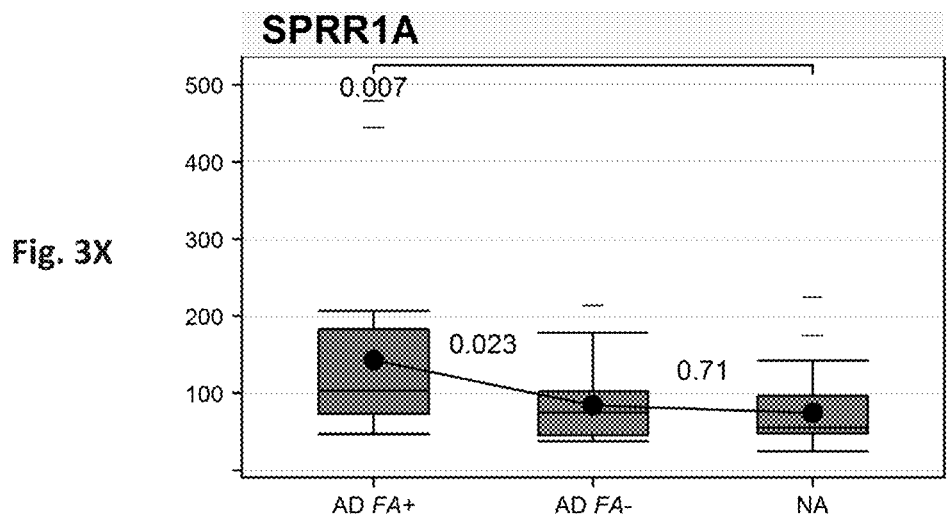
Figure 3Y:
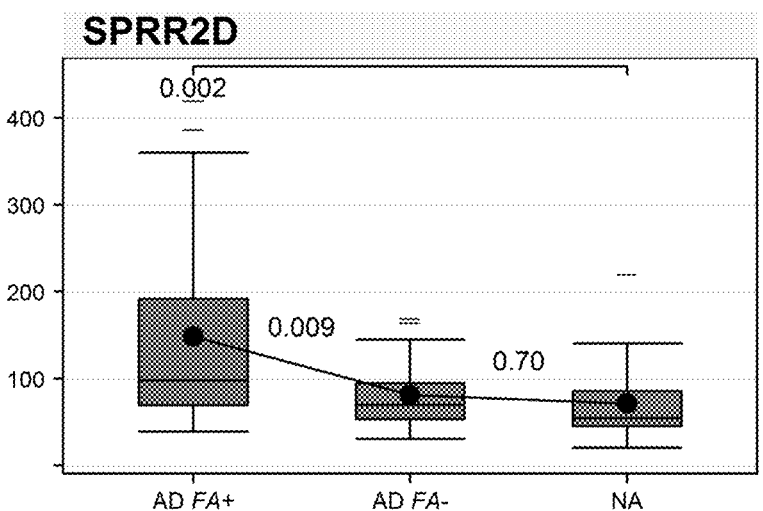
Figure 3Z:
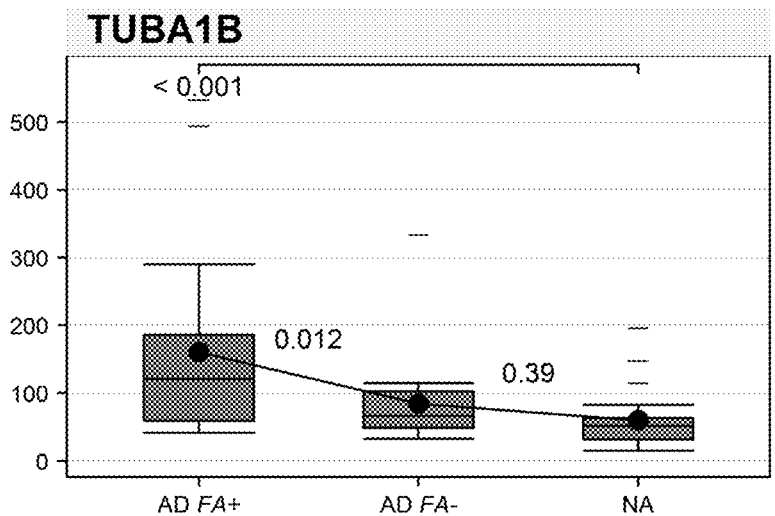
Figure 3A:
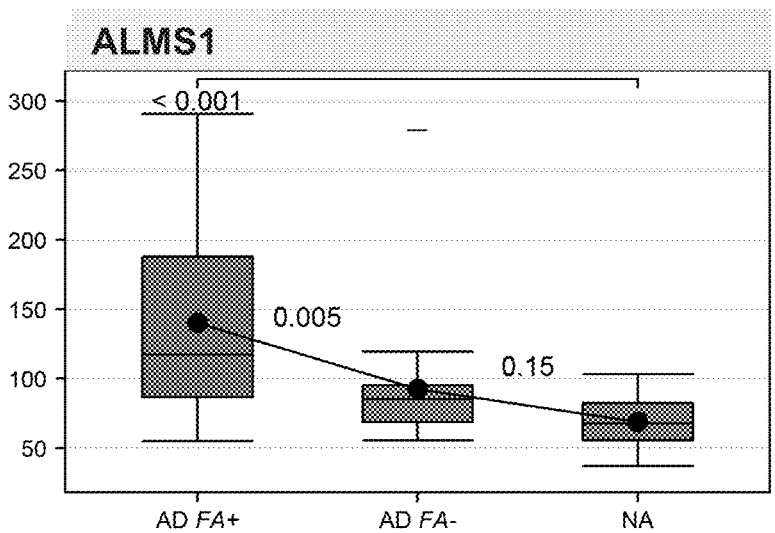
Figure 4A:
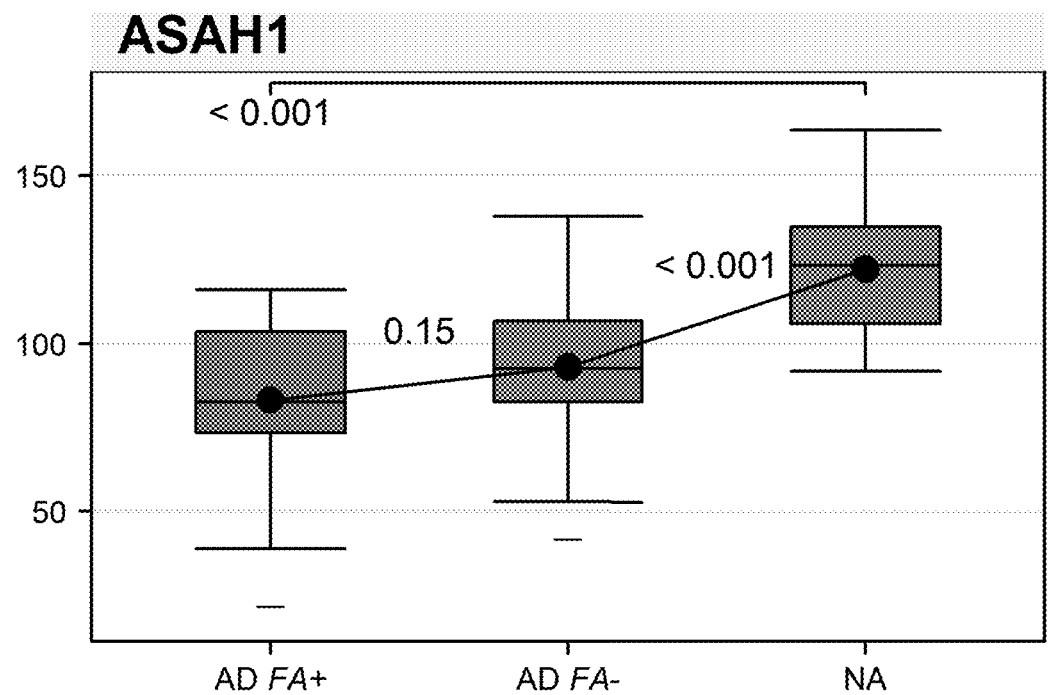
FIGS. 4A-4D show the expression of ASAH1, CSTA KRT77 and SERPINB12 proteins in non-lesinal skin. Note the complete separation for AD patients (both AD FA+ and AD FA−) vs NA for these proteins. Protein extracts were prepared from 15 skin tapes combined. In the boxplots, the solid horizontal line represents the median and the filled circle represents the mean. The box margins are the interquartile range, and the whiskers extend 1.5 times the interquartile range. Observations outside the whisker are marked by a hollow circle. The annotations are the p-values from pairwise comparisons between groups.
Figure 4B:
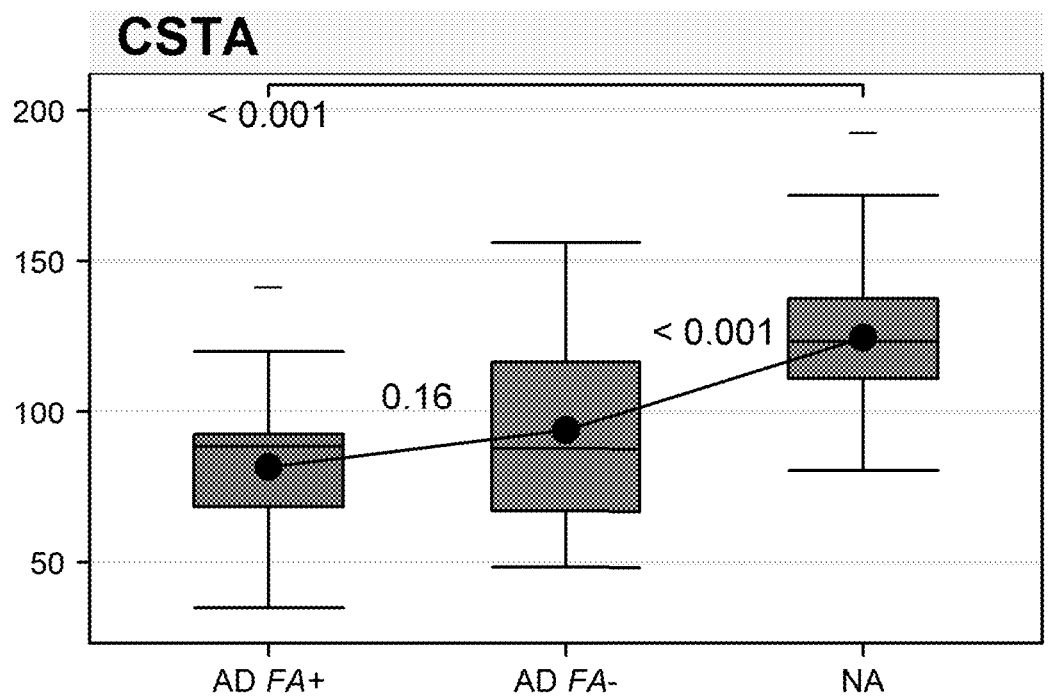
Figure 4C:
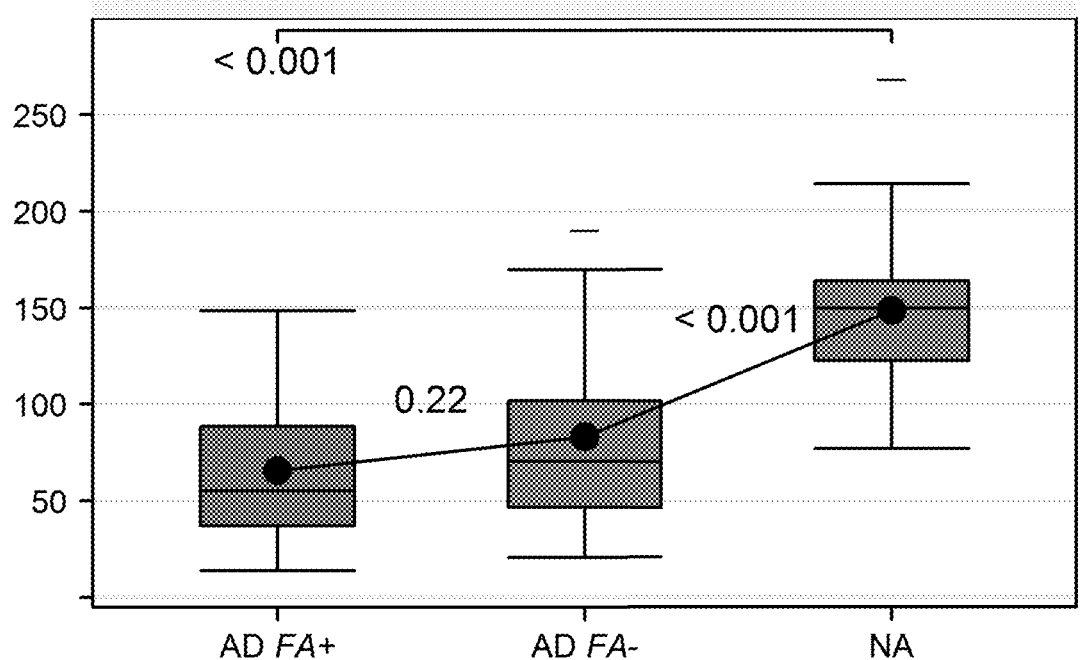
Figure 4D:
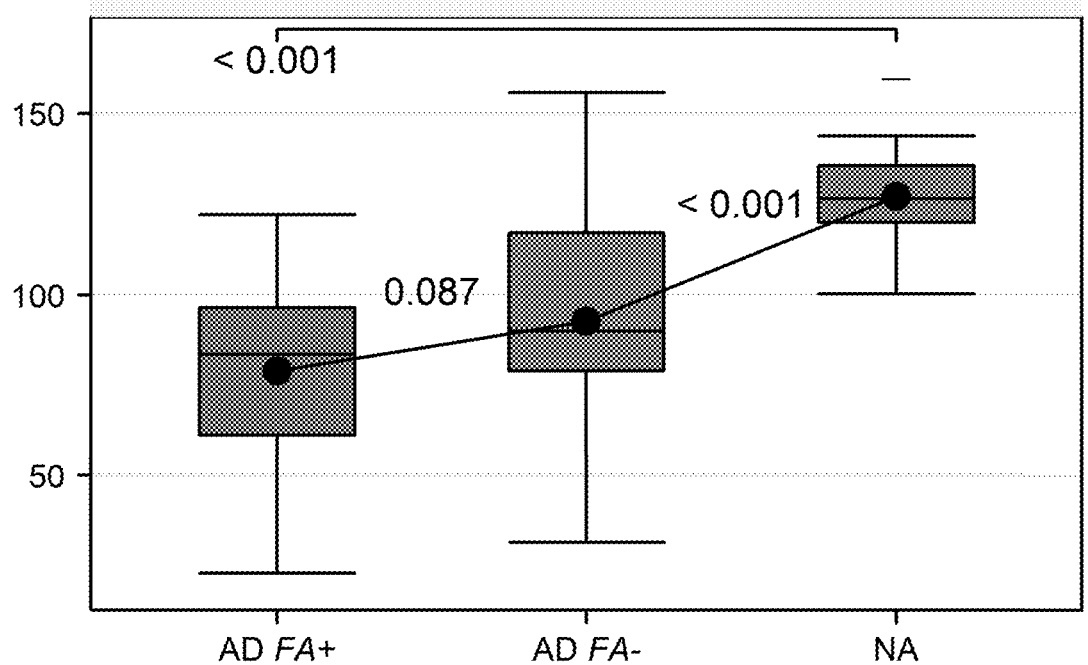

A significant decrease was also found in the amount of EOS CER at non-lesional STS #15-16 in the AD FA+ group as compared to the AD FA− group and NA controls as well as in the ratio between EOS CER and NS CER (FIG. 1C, Table 4). In contrast, no difference in EOS CER levels was found at non-lesional STS #5-6 between the AD FA+ group compared to the AD FA− and NA groups. However, the AD AD FA− groups versus the NA group are opposite in directions. This strengthens the power of the ratio between EOS CER and NS CER in comparison to just changes in each individual ceramide subclass (FIG. 1C). Similarly, there was a significant correlation between EOS CER/NS CER ratio and corresponding TEWL assessed on non-lesional and lesional skin (Table 5).

TABLE 4

Comparisons between groups for EOS CER and NS CER

| Skin Tape | | Variable | AD FA+ | AD FA− Mean (SD) | NA | AD FA+ vs AD FA− | AD FA+ vs NA Mean Difference (95% CI), p-value | AD FA− vs NA |
|---|---|---|---|---|---|---|---|---|
| Non-Lesional | #5-6 | Total EOS CER | 130.1 (95.2) | 185.0 (156.9) | 165.2 (188.6) | 54.9 (−151.5, 41.7), 0.26 | −35.1 (−128.2, 58.0), 0.45 | 19.8 (−75.7, 115.4), 0.68 |
| | | Total C18 NS CER | 1718 (1807) | 1430 (1251) | 573 (293) | 289 (−516, 1094), 0.48 | 1145 (370, 1921), 0.004 | 856 (60, 1652), 0.036 |
| | | EOS CER/NS CER ratio | 0.17 (0.22) | 0.35 (0.36) | 0.27 (0.20) | 0.17 (−0.34, −0.01), 0.043 | −0.10 (−0.26, 0.06), 0.23 | 0.08 (−0.09, 0.24), 0.37 |
| | #15-16 | Total EOS CER | 255.2 (203.2) | 462.8 (266.6) | 497.5 (326.5) | −207.6 (−379.5, −35.7), 0.019 | −242.3 (−408, −76.7), 0.005 | −34.7 (−204.7, 135.3), 0.68 |
| | | Total C18 NS CER | 1013 (1015) | 717 (343) | 456 (236) | 296 (−107, 699), 0.15 | 558 (169, 946), 0.006 | 261 (−137, 660), 0.19 |
| | | EOS CER/NS CER ratio | 0.38 (0.32) | 0.79 (0.54) | 1.23 (0.87) | −0.40 (−0.80, −0.01), 0.047 | −0.84 (−1.23, −0.46), <0.001 | −0.44 (−0.83, −0.05), 0.029 |
| Lesional | #5-6 | Total EOS CER | 98.8 (99.3) | 147.3 (154.8) | | −48.6 (−131.0, 33.8), 0.24 | | |
| | | Total C18 NS CER | 2613 (2335) | 3160 (2782) | | −546 (−2185, 1092), 0.50 | | |
| | | EOS CER/NS CER ratio | 0.09 (0.13) | 0.18 (0.26) | | −0.08 (−0.21, 0.04), 0.20 | | |
| | #15-16 | Total EOS CER | 243.4 (243.5) | 179.4 (103.9) | | 64.0 (−58.2, 186.2), 0.30 | | |
| | | Total C18 NS CER | 1693 (1204) | 1729 (966) | | −36 (−740, 667), 0.92 | | |
| | | EOS CER/NS CER ratio | 0.22 (0.25) | 0.19 (0.25) | | 0.03 (−0.12, 0.19), 0.67 | | |

TABLE 5

Correlations between EOS CER and NS CER with the corresponding TEWL

| | Non-Lesional | | Lesional | |
|---|---|---|---|---|
| Variable | Skin Tape #5-6 vs TEWL #5 | Skin Tape #15-16 vs. TEWL #15 | Skin Tape #5-6 vs TEWL Lesional | Skin Tape #15-16 vs. TEWL Lesional |
| | Pearson Correlation (95% CI), p-value | | | |
| Total EOS CER | −0.16 (−0.39, 0.10), 0.23 | −0.16 (−0.40, 0.09), 0.20 | −0.36 (−0.60, −0.05), 0.024 | −0.44 (−0.66, −0.15), 0.005 |
| Total C18 NS CER | 0.66 (0.49, 0.78), <0.001 | 0.55 (0.34, 0.70), <0.001 | 0.57 (0.31, 0.75), <0.001 | 0.56 (0.30, 0.74), <0.001 |
| EOS CER/NS CER ratio | −0.27 (−0.49, −0.02), 0.034 | −0.32 (−0.53, −0.08), 0.01 | −0.36 (−0.60, −0.05), 0.023 | 0.49 (−0.70, −0.21), 0.001 |

Abnormal Epidermal Keratin Expression in AD FA+ Skin

The epidermis is a highly organized, stratified squamous epithelium characterized by proliferation in its basal layer and terminal differentiation in the SC (Fuchs E. Epidermal differentiation: the bare essentials. J Cell Biol 1990; 111: 2807-14; Candi E. The cornified envelope: a model of cell death in the skin. Nat Rev Mol Cell Biol 2005; 6:328-40; Bikle D D, Xie Z, Tu C L. Calcium regulation of keratinocyte differentiation. Expert Rev Endocrinol Metab 2012; 7:461-72). The current results showing increased TEWL, low FLG, decreased EOS CER/NS CER ratio, and increased *S. aureus* colonization in the AD FA+ group indicate that AD FA+ skin has abnormal barrier function and lack of epidermal terminal differentiation.

Keratin (KRT) 14 are predominantly expressed by basal keratinocytes (Bragulla H H. Structure and functions of keratin proteins in simple, stratified, keratinized and cornified epithelia. J Anat 2009; 214:516-59; Lessard J C. Keratin 16 regulates innate immunity in response to epidermal barrier breach. Proc Natl Acad Sci USA 2013; 110:19537-3542). Using proteomics, the inventors examined the expression of keratins in STS samples from AD FA+, AD FA−, and NA participants. Although skin tape stripping samples only the SC and upper granular layers of the skin, a significant increase in KRT14 levels was observed in the skin of AD FA+ participants (FIG. 2B and Table 6) as compared to the other 2 groups. This is unusual, as KRT14 is predominantly expressed by undifferentiated proliferating keratinocytes. These results indicate that the superficial layer of skin in AD FA+ participants are characterized by keratinocytes that hyperproliferate impairing their ability to terminally differentiate thus accounting for the low FLG, and lipid abnormalities.

TABLE 6

Correlations between keratin expression in non-lesional skin and TEWL

| | Pearson Correlation (95% CI), p-value | |
|---|---|---|
| | TEWL AUC | TEWL 15 |
| KRT 5 | 0.46 (0.24, 0.64), <0.001 | 0.45 (0.22, 0.63), <0.001 |
| KRT 14 | 0.62 (0.44, 0.76), <0.001 | 0.58 (0.39, 0.73), <0.001 |

TABLE 6-continued

Correlations between keratin expression in non-lesional skin and TEWL

| | Pearson Correlation (95% CI), p-value | |
|---|---|---|
| | TEWL AUC | TEWL 15 |
| KRT 16 | 0.66 (0.50, 0.78), <0.001 | 0.61 (0.43, 0.75), <0.001 |

Unique Protein Expression in STS from AD FA+ and AD FA− Subjects.

A group of 27 proteins (ACTB, DSP, EEF1A1, ENO1, GDI2, GSN, GSTP1, HISTH2BK, HIST1H3, HIST1H4, KRT14, KRT16, KRT5, HSPB1, LDHA, LGALS, LGALS3, POF1B, S100A7, S100A8, S100A9, SERPINB3, SFN, SPRR1A, SPRR2D, TUB1A, and ALMS1) was determined to have a significantly increased expression in non-lesional STS proteomic analysis of AD FA+ as compared to both STS protein samples from AD FA− and NA controls (FIG. 3). Four proteins (ASAH1, CSTA, KRT77, SERPINB12) were decreased in non-lesional STS protein extracts from all AD subjects irrespective of FA as compared to NA controls (FIGS. 4A-4D). The data supports the utility of non-lesional STS protein analysis for the prediction of subjects at risk for AD and AD with FA.

Utilization of FLG Breakdown Products to Predict Subjects at Risk for AD or FA

Analysis of STS #1-2, and #3-4 (superficial skin layers) determined significantly decreased levels of FLG breakdown products in all AD subjects irrespective of FA as compared to NA controls (Table 2). In addition, significantly reduced levels of PCA (STS #1-2, #5-6) and UCA (STS #5-6) were found in FA patients with no history of AD (FAonly) as compared to NA controls (Table 7). The data suggests that FLG breakdown products analysis in the superficial skin layers can be utilized for the detection of subjects at risk for AD and at risk for FA.

TABLE 7

Comparisons between FAonly and NA for filaggrin breakdown products

| Location | Skin Tape | Variable (μg/mg) | FA only, Mean (SD) | NA, Mean (SD) | FA only vs NA, Mean Difference (95% CI), p-value |
|---|---|---|---|---|---|
| Non-Lesional | #1-2 | Pyroglutamic Acid | 22.8 (10.1) | 39.1 (16.3) | −16.3 (−26.5, −6.0), 0.0028 |
| | | Total cis-trans-UCA | 13.1 (7.0) | 17.7 (8.6) | −4.6 (−10.4, 1.2), 0.11 |
| | #5-6 | Pyroglutamic Acid | 54.3 (14.6) | 204.9 (152.7) | −150.5 (−255.9, −45.2), 0.0067 |
| | | Total cis-trans-UCA | 22.3 (5.0) | 42.8 (22.7) | −20.5 (−36.3, −4.8), 0.0124 |
| | #15-16 | Pyroglutamic Acid | 77.5 (36.5) | 76.1 (19.1) | 1.4 (−17.7, 20.5), 0.88 |
| | | Total cis-trans-UCA | 37.5 (26.8) | 39.5 (11.6) | −1.9 (−15.2, 11.3), 0.77 |

All of the documents cited herein are incorporated herein by reference.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following exemplary claims.

REFERENCES

1. Czarnowicki T. Novel concepts of prevention and treatment of atopic dermatitis through barrier and immune manipulations with implications for the atopic march. J Allergy Clin Immunol 2017; 139:1723-34.
2. Klinnert M D, Booster G, Copeland M, et al. Role of behavioral health in management of pediatric atopic dermatitis. Ann Allergy Asthma Immunol 2018; 120:42-8 e8.
3. Tran M M. Predicting the atopic march: Results from the Canadian Health Infant Longitudinal Development Study. J Allergy Clin Immunol 2018; 141:601-7.
4. Muraro A, Lemanske R F, Jr., Hellings P W, et al. Precision medicine in patients with allergic diseases: Airway diseases and atopic dermatitis-PRACTALL document of the European Academy of Allergy and Clinical Immunology and the American Academy of Allergy, Asthma & Immunology. J Allergy Clin Immunol 2016; 137:1347-58.
5. Eigenmann P A. Prevalence of IgE-mediated food allergy among children with atopic dermatiti. Pediatrics 1998; 101:e8.
6. Brough H A, Simpson A, Makinson K, et al. Peanut allergy: effect of environmental peanut exposure in children with filaggrin loss-of-function mutations. J Allergy Clin Immunol 2014; 134:867-75 e1.
7. Irvine A D. Filaggrin mutations: Associations with skin and allergic diseases. N Engl J Med 2011; 365:1315-27.
8. Lack G, Fox D, Northstone K, Golding J, Avon Longitudinal Study of P, Children Study T. Factors associated with the development of peanut allergy in childhood. N Engl J Med 2003; 348:977-85.
9. Tordesillas L, Goswami R, Benede S, et al. Skin exposure promotes a Th2-dependent sensitization to peanut allergens. J Clin Invest 2014; 124:4965-75.
10. Lin T K. Cellular changes that accompany shedding of human corneocytes. J Invest Dermatol 2012; 132:2430-9.
11. Kezic S. Levels of filaggrin degradation products are influenced by both filaggrin gentotype and atopic dermatitis severity. Allergy 2011; 66:934-40.
12. Fuchs E. Epidermal differentiation: the bare essentials. J Cell Biol 1990; 111:2807-14.
13. Candi E. The cornified envelope: a model of cell death in the skin. Nat Rev Mol Cell Biol 2005; 6:328-40.
14. Bikle D D, Xie Z, Tu C L. Calcium regulation of keratinocyte differentiation. Expert Rev Endocrinol Metab 2012; 7:461-72.

15. Bragulla H H. Structure and functions of keratin proteins in simple, stratified, keratinized and cornified epithelia. J Anat 2009; 214:516-59.
16. Lessard J C. Keratin 16 regulates innate immunity in response to epidermal barrier breach. Proc Natl Acad Sci USA 2013; 110:19537-3542.
17. Dyjack N, Goleva E, Rios C, et al. Minimally invasive skin tape strip RNA sequencing identifies novel characteristics of the type 2-high atopic dermatitis disease endotype. J Allergy Clin Immunol 2018; 141:1298-309.
18. Seidenari S. Objective assessment of the skin of children affected by atopic dermatitis: a study of pH, capacitance and TEWL in eczematous and clinically uninvolved skin. Acta Derm Venereol 1995; 75:429-33.
19. Kelleher M. Skin barrier dysfunction measured by transepidermal water loss at 2 days and 2 months predates and predicts atopic dermatitis at 1 year. J Allergy Clin Immunol 2015; 135:930-5.
20. Kelleher M M. Skin barrier impairment at birth predicts food allergy at 2 years of age. J Allergy Clin Immunol 2016; 137:1111-6.
21. Berdyshev E, Goleva E, Bronova I, et al. Lipid abnormalities in atopic skin are driven by type 2 cytokines. JCI Insight 2018; 3.
22. Broccardo C J, Mahaffey S, Schwarz J, et al. Comparative proteomic profiling of patients with atopic dermatitis based on history of eczema herpeticum infection and *Staphylococcus aureus* colonization. J Allergy Clin Immunol 2011; 127:186-93, 93 e1-11.
23. Oyoshi M K. Mechanical injury polarizes skin dendritic cells to elicit a Th2 response by inducing cutaneous thymic stromal lymphopoietin expression. J Allergy Clin Immunol 2010; 126:976-84.
24. Walker M T, Green J E, Ferrie R P, Queener A M, Kaplan M H, Cook-Mills J M. Mechanism for initiation of food allergy: Dependence on skin barrier mutations and environmental allergen costimulation. J Allergy Clin Immunol 2018; 141:1711-25 e9.
25. Flohr C, Perkin M, Logan K, et al. Atopic dermatitis and disease severity are the main risk factors for food sensitization in exclusively breastfed infants. J Invest Dermatol 2014; 134:345-50.
26. Brown S J, Asai Y, Cordell H J, et al. Loss-of-function variants in the filaggrin gene are a significant risk factor for peanut allergy. J Allergy Clin Immunol 2011; 127:661-7.
27. Brough H A. Atopic dermatitis increases the impact of exposure to peanut antigen in dust on peanut sensitization and allergy. J Allergy Clin Immunol 2015; 135:164-70.
28. Thyssen J P. Causes of epidermal filaggrin reduction and their role in the pathogenesis of atopic dermatitis. J Allergy Clin Immunol 2014; 134:792-9.
29. Howell M D. Cytokine modulation of AD filaggrin skin expression. J Allergy Clin Immunol 2007; 120:150-5.
30. Kim B E. Loricrin and involucrin expression is downregulated by Th2 cytokines through STAT-6. Clin Immunol 2008; 126:332-7.
31. De Benedetto A, Rafaels N M, McGirt L Y, et al. Tight junction defects in patients with atopic dermatitis. J Allergy Clin Immunol 2011; 127:773-86 e1-7.
32. Pendaries V, Malaisse J, Pellerin L, et al. Knockdown of filaggrin in a three-dimensional reconstructed human epidermis impairs keratinocyte differentiation. J Invest Dermatol 2014; 134:2938-46.
33. Vavrova K, Henkes D, Struver K, et al. Filaggrin deficiency leads to impaired lipid profile and altered acidification pathways in a 3D skin construct. J Invest Dermatol 2014; 134:746-53.
34. Gruber R, Elias P M, Crumrine D, et al. Filaggrin genotype in ichthyosis vulgaris predicts abnormalities in epidermal structure and function. Am J Pathol 2011; 178:2252-63.
35. Elias P M, Wakefield J S. Mechanisms of abnormal lamellar body secretion and the dysfunctional skin barrier in patients with atopic dermatitis. J Allergy Clin Immunol 2014; 134:781-91 e1.
36. Marekov L N, Steinert P M. Ceramides are bound to structural proteins of the human foreskin epidermal cornified cell envelope. J Biol Chem 1998; 273:17763-70.
37. Nakatsuji T, Chen T H, Two A M, et al. *Staphylococcus aureus* Exploits Epidermal Barrier Defects in Atopic Dermatitis to Trigger Cytokine Expression. J Invest Dermatol 2016; 136:2192-200.
38. Williams M R, Nakatsuji T, Sanford J A, Vrbanac A F, Gallo R L. *Staphylococcus aureus* Induces Increased Serine Protease Activity in Keratinocytes. J Invest Dermatol 2017; 137:377-84.
39. Kennedy E A. Skin microbiome before development of atopic dermatitis: Early colonization with commensal staphylococci at 2 months is associated with a lower risk of atopic dermatitis in 1 year. J Allergy Clin Immunol 2017; 139:166-72.
40. Meylan P, Lang C, Mermoud S, et al. Skin Colonization by *Staphylococcus aureus* Precedes the Clinical Diagnosis of Atopic Dermatitis in Infancy. J Invest Dermatol 2017; 137:2497-504.
41. Nakatsuji T, Chen T H, Narala S, et al. Antimicrobials from human skin commensal bacteria protect against *Staphylococcus aureus* and are deficient in atopic dermatitis. Sci Transl Med 2017; 9.
42. Ong P Y, Ohtake T, Brandt C, et al. Endogenous antimicrobial peptides and skin infections in atopic dermatitis. N Engl J Med 2002; 347:1151-60.
43. Kim J, Kim B E, Lee J, et al. Epidermal thymic stromal lymphopoietin predicts the development of atopic dermatitis during infancy. J Allergy Clin Immunol 2016; 137:1282-5 e4.
44. Kobayashi T, Glatz M, Horiuchi K, et al. Dysbiosis and *Staphylococcus aureus* Colonization Drives Inflammation in Atopic Dermatitis. Immunity 2015; 42:756-66.
45. Jones A L. Food allergy is associated with *Staphylococcus aureus* colonization in children with atopic dermatitis. J Allergy Clin Immunol 2016; 137:1247-8.
46. Lowe A J, Su J C, Allen K J, et al. A randomized trial of a barrier lipid replacement strategy for the prevention of atopic dermatitis and allergic sensitization: the PEBBLES pilot study. Br J Dermatol 2018; 178:e19-e21.
47. Keet C A. Emerging therapies for food allergy. J Clin Invest 2014; 124:1880-6.
48. Omori-Miyake M, Yamashita M, Tsunemi Y, Kawashima M, Yagi J. In vitro assessment of IL-4- or IL-13-mediated changes in the structural components of keratinocytes in mice and humans. J Invest Dermatol 2014; 134:1342-50.
49. Hamilton J D, Suarez-Farinas M, Dhingra N, et al. Dupilumab improves the molecular signature in skin of patients with moderate-to-severe atopic dermatitis. J Allergy Clin Immunol 2014; 134:1293-300.
50. Beck L A, Thaci D, Hamilton J D, et al. Dupilumab treatment in adults with moderate-to-severe atopic dermatitis. N Engl J Med 2014; 371:130-9.
51. Beck L A, Boguniewicz M, Hata T, et al. Phenotype of atopic dermatitis subjects with a history of eczema herpeticum. J Allergy Clin Immunol 2009; 124:260-9, 9 e1-7.

52. Roberts G, Lack G. Diagnosing peanut allergy with skin prick and specific IgE testing. J Allergy Clin Immunol 2005; 115:1291-6.
53. Simpson E L. Patients with atopic dermatitis colonized with *Staphylococcus aureus* have a distinct phenotype and endotype. J Invest Dermatol 2018.
54. Severity scoring of atopic dermatitis: the SCORAD index. Consensus Report of the European Task Force on Atopic Dermatitis. Dermatology 1993; 186:23-31.
55. Emerson R M, Charman C R, Williams H C. The Nottingham Eczema Severity Score: preliminary refinement of the Rajka and Langeland grading. Br J Dermatol 2000; 142:288-97.
56. Phan N Q, Blome C, Fritz F, et al. Assessment of pruritus intensity: prospective study on validity and reliability of the visual analogue scale, numerical rating scale and verbal rating scale in 471 patients with chronic pruritus. Acta Derm Venereol 2012; 92:502-7.
57. Leshe Y A. What the Eczema Area and Severity Index score tells us about the severity of atopic dermatitis: An interpretability study. Br J Dermatol 2015; 172:1353-7.
58. Joo K M, Han J Y, Son E D, et al. Rapid, simultaneous and nanomolar determination of pyroglutamic acid and cis-/trans-urocanic acid in human *Stratum corneum* by hydrophilic interaction liquid chromatography (HILIC)-electrospray ionization tandem mass spectrometry. J Chromatogr B Analyt Technol Biomed Life Sci 2012; 897:55-63.
59. Bligh E G, Dyer W J. A rapid method of total lipid extraction and purification. Can J Biochem Physiol 1959; 37:911-7.
60. Bolger A M, Lohse M, Usadel B. Trimmomatic: a flexible trimmer for Illumina sequence data. Bioinformatics 2014; 30:2114-20.
61. Embree M, Liu J K, Al-Bassam M M, Zengler K. Networks of energetic and metabolic interactions define dynamics in microbial communities. Proc Natl. Acad Sci USA 2015; 112:15450-5.
62. A. Thompson, J. Schafer, K. Kuhn, S. Kienle, J. Schwarz, G. Schmidt, et al. Tandem mass tags: a novel quantification strategy for comparative analysis of complex protein mixtures by MS/MS Anal Chem, 75 (2003), pp. 1895-1904.

What is claimed:

1. A method to identify a subject at risk of developing a food allergy comprising:
    a. obtaining a skin sample from the subject, wherein the skin sample is a non-lesional skin sample from the subject;
    b. determining a level of urocanic acid (UCA), pyroglutamic (PCA) or a combination thereof; wherein the skin sample is obtained by a skin tape stripping method comprising: applying an adhesive tape to a target area of the skin of the subject in a manner sufficient to isolate an epidermal sample adhering to the adhesive tape, wherein the epidermal sample comprises cells from *Stratum corneum* of the subject, wherein the tape comprises a rubber adhesive; extracting the epidermal sample comprising the UCA, PCA or combination thereof adhering to the adhesive tape with a cell scraper comprising thermoplastic elastomer material in a solvent of about 5% to about 30% alcohol in water; and
    c. comparing the level of UCA PCA or a combination thereof in the skin sample to levels of UCA, PCA, or a combination thereof from a control sample wherein a statistically reduced level of UCA, PCA or a combination thereof in the skin sample as compared to the levels in the control sample identifies the subject as being at risk of developing a food allergy, and wherein the control sample is from one or more non-atopic (NA) subjects.

2. The method of claim 1 further comprising determining a ratio of esterified ω-hydroxy fatty acid sphingosine ceramides (EOS CER) to nonhydroxy fatty acid sphingosine ceramides (NS CER) in the skin sample from the subject and in the skin sample from the control; and comparing the ratio of EOS CER to NS CER in the skin sample to the ratio in the control sample wherein a decreased ratio in the skin sample as compared to the control sample further identifies the subject as being at risk of developing a food allergy.

3. The method of claim 1, wherein the skin sample comprises layers 1, 2 or a sum of layers 1 and 2 from *Stratum corneum* of the subject.

4. The method of claim 1, wherein the skin sample comprises layers 3, 4 or a sum of layers 3 and 4 from *stratum corneum* of the subject.

5. The method of claim 1, further comprising determining an expression level of the UCA, PCA or a combination thereof in the epidermal sample.

6. The method of claim 1, wherein 4 or fewer skin tapes are applied to the subject.

7. The method of claim 1, wherein the subject identified as at risk of having a food allergy is administered a pharmaceutical composition comprising a compound selected from the group consisting of corticosteroids, leukotriene antagonists, anti-cytokine antibodies, anti-cytokine receptor antibodies, anti-IgE antibody, anti-interleukin 14 (IL14) antibodies, anti-interleukin 13 (IL13) antibodies, JAK kinase inhibitors, JAK/STAT inhibitors, antibiotics, a phosphodiesterase inhibitor, a cream comprising filaggrin or components thereof, ceramide rich emollients, and combinations thereof.

8. The method of claim 7, wherein the pharmaceutical composition is administered by an administration route selected from the group consisting of local administration, topical administration, and injection.

9. The method of claim 1, wherein the food allergy is selected from the group consisting of a peanut allergy, a milk allergy, an egg allergy, a wheat allergy, a tree nut allergy and a combination thereof.

10. The method of claim 1 wherein the subject is less than 18 years of age.

11. The method of claim 1, wherein the subject does not have atopic dermatitis.

* * * * *